(12) United States Patent
Denolf et al.

(10) Patent No.: US 9,873,886 B2
(45) Date of Patent: Jan. 23, 2018

(54) BRASSICA ROD1 GENE SEQUENCES AND USES THEREOF

(71) Applicant: Bayer CropScience NV, Diegem (BE)

(72) Inventors: Peter Denolf, Velzeke (BE); Michel Van Thournout, Sint-Michiels (BE); Stephane Bourot, Comines (BE)

(73) Assignee: Bayer CropScience NV, Diegem (BE)

( * ) Notice: Subject to any disclaimer, the term of this patent is extended or adjusted under 35 U.S.C. 154(b) by 22 days.

(21) Appl. No.: 14/409,711

(22) PCT Filed: Jul. 4, 2013

(86) PCT No.: PCT/EP2013/064186
§ 371 (c)(1),
(2) Date: Dec. 19, 2014

(87) PCT Pub. No.: WO2014/006158
PCT Pub. Date: Jan. 9, 2014

(65) Prior Publication Data
US 2015/0143573 A1 May 21, 2015

Related U.S. Application Data

(60) Provisional application No. 61/669,370, filed on Jul. 9, 2012.

(30) Foreign Application Priority Data

Jul. 6, 2012 (EP) .................................. 12175303

(51) Int. Cl.
| | |
|---|---|
| *A01H 5/10* | (2006.01) |
| *C12N 15/82* | (2006.01) |
| *A01H 1/04* | (2006.01) |
| *C12Q 1/68* | (2006.01) |
| *C12N 9/12* | (2006.01) |
| *C11B 1/10* | (2006.01) |
| *C11C 3/00* | (2006.01) |
| *C11B 1/00* | (2006.01) |
| *C07K 14/415* | (2006.01) |
| *A23K 10/30* | (2016.01) |

(52) U.S. Cl.
CPC .......... *C12N 15/8247* (2013.01); *A01H 1/04* (2013.01); *A01H 5/10* (2013.01); *A23K 10/30* (2016.05); *C07K 14/415* (2013.01); *C11B 1/00* (2013.01); *C11B 1/10* (2013.01); *C11C 3/00* (2013.01); *C11C 3/003* (2013.01); *C12N 9/1288* (2013.01); *C12N 15/8218* (2013.01); *C12Q 1/6895* (2013.01); *C12Y 207/08002* (2013.01)

(58) Field of Classification Search
None
See application file for complete search history.

(56) References Cited

U.S. PATENT DOCUMENTS

2005/0039233 A1* 2/2005 Yao .......................... A01H 5/10
800/281

FOREIGN PATENT DOCUMENTS

WO WO 2009/111587 * 9/2009 ............... A01H 5/00

OTHER PUBLICATIONS

An, Yong-Qiang, et al., Conserved Expression of the *Arabidopsis* ACT7 and ACT3 Actin Subclass in Organ Primordia and Mature Pollen, The Plant Cell, Jan. 1996, pp. 15-30, vol. 8.
Azpiroz-Leehan, Ricardo, et al., T-DNA insertion mutagenesis in *Arabidops* going back and forth, TIG, Apr. 1997, pp. 152-156, vol. 13, No. 4.
Broun, Pierre, et al., Genetic Engineering of Plant Lipids, Annu. Rev. Nutr., 1999, pp. 197-216, vol. 19.
Browse, John, Glycerolipid Synthesis: Biochemistry and Regulation, Annu. Rev. Plant Physiol. Plant Mol. Bioi. 1991, pp. 467-506, vol. 42.
Chaubet, Nicole, et al., Nucleotide sequences of two corn histone H3 genes. Genomic organization of the corn histone H3 and H4 genes, Plant Molecular Biology, 1986, pp. 253-263, vol. 6.
Christensen, Alan H., et al., Maize polyubiquitin genes: structure, thermal perturbation of expression and transcript splicing, and promoter activity following transfer to protoplasts by electroporation, Plant Molecular Biology, 1992, pp. 675-689, vol. 18.
De Pater, B. Sylvia, et al., The promoter of the rice gene GOS2 is active in various different monocot tissues and binds rice nuclear factor ASF-I, The Plant Journal, 1992, pp. 837-844, vol. 2(6).
Depicker, A., et al., Nopaline Synthase: Transcript Mapping and DNA Sequence, Journal of Molecular and Applied Genetics, 1982, pp. 561-573.
Gunstone, F.D., Movements Towards Tailor-Made Fats, Prog. Lipid Res., 1998, pp. 277-305, vol. 37, No. 5.
Harpster, Mark H., et al., Relative strengths of the 35S califlower mosaic virus, 1', 2', and nopaline synthase promoters, Mol Gen Genet, 1988, pp. 182-190, vol. 212.
Henikoff, Steven, et al., Tilling. Traditional Mutagenesis Meets Functional Genomics, Plant Physiology, Jun. 2004, pp. 630-636, vol. 135.
Hudspeth, Richard L., et al., Structure and expression of the maize gene encoding the phosphoenolpyruvate carboxylase isozyme involved in C4 photosynthesis, Plant Molecular Biology, 1989, pp. 579-589, vol. 12.
Jaworski, Jan, et al., Industrial oils from transgenic plants, Current Opinion in Plant Biology, 2003, pp. 178-184, vol. 6.
Keil, Michael, et al., Both wound-inducible and tuber-specific expression are mediated by the promoter of a single member of the potato proteinase inhibitor II gene family, The EMBO Journal, 1989, pp. 1323-1330, vol. 8 No. 5.
Keller, Beat, et al., Glycine-rich cell wall proteins in bean: gene structure and association of the protein with the vascular system, The EMBO Journal, 1988, pp. 3625-3633, vol. 7 No. 12.
Li, Xin, et al., Reverse genetics by fast neutron mutagenesis in higher plants, Funct Integr Genomics, 2002, pp. 254-258, vol. 2.

(Continued)

*Primary Examiner* — Elizabeth McElwain

(57) ABSTRACT

The present invention relates to *Brassica juncea* ROD1 nucleic acid sequences and proteins and the use thereof to create plants with increased levels of C18:1 and reduced levels of saturated fatty acids in the seeds.

8 Claims, No Drawings

(56) References Cited

OTHER PUBLICATIONS

Li, Xin, et al., A fast neutron deletion mutagenesis-based reverse genetics system for plants, The Plant Journal, 2001, pp. 235-242, vol. 27(3).
Lu, Chaofu, et al., An enzyme regulating triacylglycerol composition is encoded by the ROD1 gene of *Arabidopsis*, PNAS Early Edition, pp. 1-6.
McCallum, Claire M., et al., Targeting Induced Local Lesions IN Genomes (TILLING) for Plant Functional Genomics, Plant Physiology, Jun. 2000, pp. 439-442, vol. 123.
McCallum, Claire M., et al., Targeted screening for induced mutations, Nature Biotechnology, Apr. 2000, pp. 455-457, vol. 18.

\* cited by examiner

SEQUENCE LISTING

```
<160> NUMBER OF SEQ ID NOS: 14

<210> SEQ ID NO 1
<211> LENGTH: 1142
<212> TYPE: DNA
<213> ORGANISM: Brassica juncea
<220> FEATURE:
<221> NAME/KEY: CDS
<222> LOCATION: (238)..(1080)

<400> SEQUENCE: 1
acaagtaaag cccaacaaag acagatgaga aaatagcaaa gacttgcgta aacgtcgctc      60
tcaaacctca tctcatactc atcgttttcg tatgagtttt tgtagcccaa acaatcttcc     120
tttctacagt ttataatata agaaacaata cttccttcgt aatctccgcc tcgtatctct     180
tatataactc atctctctaa acctaaaaaa tgttcctctc cgttaaatct aacggtc       237 atg tca act aat acc gtc gtc cct ctc cgt cgc aga tct aac gga aat      285
Met Ser Thr Asn Thr Val Val Pro Leu Arg Arg Arg Ser Asn Gly Asn
1               5                   10                  15 cac act aac ggc gag gcc ttt aac gga atg gag aac att gtc aag aaa      333
His Thr Asn Gly Glu Ala Phe Asn Gly Met Glu Asn Ile Val Lys Lys
                20                  25                  30 acc gac gac tgc tac acc aac ggc aac gga gga gta gag aga agc aaa      381
Thr Asp Asp Cys Tyr Thr Asn Gly Asn Gly Gly Val Glu Arg Ser Lys
            35                  40                  45
```

```
gcc tcg ttt ctg aca tgg acc atg cgt gac gct gtc tac gta gcg aga    429
Ala Ser Phe Leu Thr Trp Thr Met Arg Asp Ala Val Tyr Val Ala Arg
    50                  55                  60 tac cat tgg ata ccg tgt ttc ttt gcg gtc gga gtt ctg ttc ttt atg    477
Tyr His Trp Ile Pro Cys Phe Phe Ala Val Gly Val Leu Phe Phe Met
65                  70                  75                  80 ggg gtt gag tac acg ctc cag atg gtt ccg gcg aag tct gag ccg ttc    525
Gly Val Glu Tyr Thr Leu Gln Met Val Pro Ala Lys Ser Glu Pro Phe
                85                  90                  95 gat att ggg ttt gtg gcc acg cgc tct ctg aac cgc gtc ttg gcg agt    573
Asp Ile Gly Phe Val Ala Thr Arg Ser Leu Asn Arg Val Leu Ala Ser
            100                 105                 110 tca ccg gat ctt aac acc ctt tta gcg gct cta aac acg gta ttc gta    621
Ser Pro Asp Leu Asn Thr Leu Leu Ala Ala Leu Asn Thr Val Phe Val
        115                 120                 125 gcg atg caa acg acg tat att gta tgg aca tgg ttg atg gaa gga aga    669
Ala Met Gln Thr Thr Tyr Ile Val Trp Thr Trp Leu Met Glu Gly Arg
    130                 135                 140 cca cga gcc act atc tcg gct tgc ttc atg ttt act tgt cgc ggc att    717
Pro Arg Ala Thr Ile Ser Ala Cys Phe Met Phe Thr Cys Arg Gly Ile
145                 150                 155                 160 ctt ggt tac tct act cag ctc cct cta cca cag gat ttt tta gga tca    765
Leu Gly Tyr Ser Thr Gln Leu Pro Leu Pro Gln Asp Phe Leu Gly Ser
                165                 170                 175 gga gtt gat ttt ccg gtg gga aac gtc tca ttc ttc ctc ttc tat tct    813
Gly Val Asp Phe Pro Val Gly Asn Val Ser Phe Phe Leu Phe Tyr Ser
            180                 185                 190 ggc cac gta gcc ggt tca atg atc gca tcc ttg gac atg agg aga atg    861
Gly His Val Ala Gly Ser Met Ile Ala Ser Leu Asp Met Arg Arg Met
        195                 200                 205 cag agg ttg aga cta gcg atg ctt ttt gac atc ctc aac ata tta caa    909
Gln Arg Leu Arg Leu Ala Met Leu Phe Asp Ile Leu Asn Ile Leu Gln
    210                 215                 220 tcg atc aga ctg ctc ggg acg aga gga cac tac acg atc gat ctt gcg    957
Ser Ile Arg Leu Leu Gly Thr Arg Gly His Tyr Thr Ile Asp Leu Ala
225                 230                 235                 240 gtc gga gtt ggc gct ggg att ctc ttt gac tca ttg gcc ggg aag tac   1005
Val Gly Val Gly Ala Gly Ile Leu Phe Asp Ser Leu Ala Gly Lys Tyr
                245                 250                 255 gaa gag atg atg agc aag aga cac aat tta gcc aat ggt ttt agt ttg   1053
Glu Glu Met Met Ser Lys Arg His Asn Leu Ala Asn Gly Phe Ser Leu
            260                 265                 270 att tct aaa gac tcg cta gtc aat taa tcttttgttt tcattttaaa         1100
Ile Ser Lys Asp Ser Leu Val Asn
        275                 280 tgattagttg aacttgaaca tatttgattt agttaaagac tt                    1142

<210> SEQ ID NO 2
<211> LENGTH: 280
<212> TYPE: PRT
<213> ORGANISM: Brassica juncea

<400> SEQUENCE: 2

Met Ser Thr Asn Thr Val Val Pro Leu Arg Arg Arg Ser Asn Gly Asn
1               5                   10                  15

His Thr Asn Gly Glu Ala Phe Asn Gly Met Glu Asn Ile Val Lys Lys
            20                  25                  30

Thr Asp Asp Cys Tyr Thr Asn Gly Asn Gly Gly Val Glu Arg Ser Lys
        35                  40                  45
```

```
Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280

<210> SEQ ID NO 3
<211> LENGTH: 936
<212> TYPE: DNA
<213> ORGANISM: Brassica juncea
<220> FEATURE:
<221> NAME/KEY: CDS
<222> LOCATION: (65)..(907)
<220> FEATURE:
<221> NAME/KEY: misc_feature
<222> LOCATION: (540)..(541)
<223> OTHER INFORMATION: n is a, c, g, or t

<400> SEQUENCE: 3
gtatctctta tataactcat ctctctaaac atagatatgt tcctctccgt taaatctaac    60 ggtc atg tca act aat acc gtc gtc cct ctc cgt cgc aga tct aac gga   109
     Met Ser Thr Asn Thr Val Val Pro Leu Arg Arg Arg Ser Asn Gly
     1               5                   10                  15 tat cac agt aac ggc gtg gcc ttt aac gga atg gag aac att gtc aag   157
Tyr His Ser Asn Gly Val Ala Phe Asn Gly Met Glu Asn Ile Val Lys
                20                  25                  30 aaa aca gac gac tgc tac acc aac ggc aac gga gga gga ggg aag agc   205
Lys Thr Asp Asp Cys Tyr Thr Asn Gly Asn Gly Gly Gly Gly Lys Ser
            35                  40                  45 aag gcg tcg ttt ctg aca tgg acc atg cgc gac gct gtc tac gtg gcg   253
Lys Ala Ser Phe Leu Thr Trp Thr Met Arg Asp Ala Val Tyr Val Ala
        50                  55                  60
```

| | | | | | | | | | | | | | | | | |
|---|---|---|---|---|---|---|---|---|---|---|---|---|---|---|---|---|
|aga|tac|cat|tgg|ata|ccg|tgt|ttc|ttt|gcg|gtc|gga|gtt|ctg|ttc|ttt|301|
|Arg|Tyr|His|Trp|Ile|Pro|Cys|Phe|Phe|Ala|Val|Gly|Val|Leu|Phe|Phe| |
| |65| | | |70| | | |75| | | | | | | |
|atg|ggc|gtt|gag|tat|acg|ctc|cag|atg|gtt|ccg|gcg|aag|tct|gag|ccg|349|
|Met|Gly|Val|Glu|Tyr|Thr|Leu|Gln|Met|Val|Pro|Ala|Lys|Ser|Glu|Pro| |
|80| | | | |85| | | |90| | | |95| | | |
|ttc|gat|att|ggg|ttt|gtg|gcc|acg|cgc|tct|ctg|aac|cgc|gtc|ttg|gcg|397|
|Phe|Asp|Ile|Gly|Phe|Val|Ala|Thr|Arg|Ser|Leu|Asn|Arg|Val|Leu|Ala| |
| | | |100| | | | |105| | | | |110| | | |
|agt|tca|ccg|gat|ctt|aac|acc|ctt|tta|gcg|gct|cta|aac|acg|gta|ttc|445|
|Ser|Ser|Pro|Asp|Leu|Asn|Thr|Leu|Leu|Ala|Ala|Leu|Asn|Thr|Val|Phe| |
| | | |115| | | | |120| | | | |125| | | |
|gta|gcg|atg|caa|acg|acg|tat|att|gta|tgg|aca|tgg|ttg|atg|gaa|gga|493|
|Val|Ala|Met|Gln|Thr|Thr|Tyr|Ile|Val|Trp|Thr|Trp|Leu|Met|Glu|Gly| |
| | |130| | | | |135| | | | |140| | | | |
|aga|cca|cga|gcc|act|atc|tct|gct|tgc|ttt|atg|ttt|act|tgt|cgc|gnn|541|
|Arg|Pro|Arg|Ala|Thr|Ile|Ser|Ala|Cys|Phe|Met|Phe|Thr|Cys|Arg|Xaa| |
| |145| | | | |150| | | | |155| | | | | |
|att|ctt|ggt|tac|tct|act|cag|ctc|cct|ctc|cca|cag|gat|ttt|tta|gga|589|
|Ile|Leu|Gly|Tyr|Ser|Thr|Gln|Leu|Pro|Leu|Pro|Gln|Asp|Phe|Leu|Gly| |
|160| | | | |165| | | | |170| | | | |175| |
|tca|gga|gtt|gat|ttt|cca|gtg|gga|aac|gtc|tca|ttc|ttc|ctc|ttc|tat|637|
|Ser|Gly|Val|Asp|Phe|Pro|Val|Gly|Asn|Val|Ser|Phe|Phe|Leu|Phe|Tyr| |
| | | | |180| | | | |185| | | | |190| | |
|tct|ggt|cac|gtc|gcc|ggt|tca|atg|atc|gca|tcc|ttg|gac|atg|agg|aga|685|
|Ser|Gly|His|Val|Ala|Gly|Ser|Met|Ile|Ala|Ser|Leu|Asp|Met|Arg|Arg| |
| | | |195| | | | |200| | | | |205| | | |
|atg|cgg|agg|ttg|aga|cta|gcg|atg|ctt|ttt|gac|atc|ctc|aac|gta|tta|733|
|Met|Arg|Arg|Leu|Arg|Leu|Ala|Met|Leu|Phe|Asp|Ile|Leu|Asn|Val|Leu| |
| |210| | | | |215| | | | |220| | | | | |
|caa|tct|atc|agg|ctg|ctc|ggg|aca|aga|gga|cat|tac|acg|att|gat|ctt|781|
|Gln|Ser|Ile|Arg|Leu|Leu|Gly|Thr|Arg|Gly|His|Tyr|Thr|Ile|Asp|Leu| |
|225| | | | |230| | | | |235| | | | | | |
|gcg|gtc|gga|gtt|ggc|gct|ggg|att|ctc|ttt|gac|tct|ttg|gcc|ggg|aag|829|
|Ala|Val|Gly|Val|Gly|Ala|Gly|Ile|Leu|Phe|Asp|Ser|Leu|Ala|Gly|Lys| |
|240| | | | |245| | | | |250| | | | |255| |
|tac|gaa|gag|atg|atg|agc|aag|aga|cac|aat|tta|gcc|aat|ggt|ttt|agt|877|
|Tyr|Glu|Glu|Met|Met|Ser|Lys|Arg|His|Asn|Leu|Ala|Asn|Gly|Phe|Ser| |
| | | |260| | | | |265| | | | |270| | | |
|ttg|att|tcg|aaa|gac|tcg|cta|gtc|aat|taa|tcttttgttt|tcattttaaa| | | | |927|
|Leu|Ile|Ser|Lys|Asp|Ser|Leu|Val|Asn| | | | | | | | |
| | | |275| | | | |280| | | | | | | | |
|tgattagtt| | | | | | | | | | | | | | | |936|

```
<210> SEQ ID NO 4
<211> LENGTH: 280
<212> TYPE: PRT
<213> ORGANISM: Brassica juncea
<220> FEATURE:
<221> NAME/KEY: misc_feature
<222> LOCATION: (159)..(159)
<223> OTHER INFORMATION: The 'Xaa' at location 159 stands for Glu, Asp,
      Gly, Ala, or Val.

<400> SEQUENCE: 4
```

Met Ser Thr Asn Thr Val Val Pro Leu Arg Arg Arg Ser Asn Gly Tyr
1               5                   10                  15

His Ser Asn Gly Val Ala Phe Asn Gly Met Glu Asn Ile Val Lys Lys
            20                  25                  30

Thr Asp Asp Cys Tyr Thr Asn Gly Asn Gly Gly Gly Gly Lys Ser Lys
        35                  40                  45

```
Ala Ser Phe Leu Thr Trp Thr Met Arg Asp Ala Val Tyr Val Ala Arg
     50                  55                  60

Tyr His Trp Ile Pro Cys Phe Phe Ala Val Gly Val Leu Phe Phe Met
 65                  70                  75                  80

Gly Val Glu Tyr Thr Leu Gln Met Val Pro Ala Lys Ser Glu Pro Phe
                 85                  90                  95

Asp Ile Gly Phe Val Ala Thr Arg Ser Leu Asn Arg Val Leu Ala Ser
                100                 105                 110

Ser Pro Asp Leu Asn Thr Leu Leu Ala Ala Leu Asn Thr Val Phe Val
            115                 120                 125

Ala Met Gln Thr Thr Tyr Ile Val Trp Thr Trp Leu Met Glu Gly Arg
        130                 135                 140

Pro Arg Ala Thr Ile Ser Ala Cys Phe Met Phe Thr Cys Arg Xaa Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Arg Arg Leu Arg Leu Ala Met Leu Phe Asp Ile Leu Asn Val Leu Gln
210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280

<210> SEQ ID NO 5
<211> LENGTH: 1059
<212> TYPE: DNA
<213> ORGANISM: Brassica juncea
<220> FEATURE:
<221> NAME/KEY: CDS
<222> LOCATION: (242)..(1057)

<400> SEQUENCE: 5
aatataaaaa gaacttaaca acatgttggt acaaaattaa agtaaagccc aacaagaga       60 gaaacaaag aaaaaaaata ataaggcaaa gactttgcgt aaacgtagct ctcgaaactc      120
aatactcatc gttttcgtat gaattttttgt agaccaaaca atcttccttc cacagttcac    180
aaaataaaaa caatacctcc ttcgaaatct ctgcctctta tagaactcat ctctgacgct    240 t atg tca act gaa act agc gtc cct ctc cgt cgc aga tct acc tct ctt    289
  Met Ser Thr Glu Thr Ser Val Pro Leu Arg Arg Arg Ser Thr Ser Leu
   1               5                  10                  15 aac gga cat cac tct aac gac gtc gcc ttt gac gga acc gtc cca tta    337
Asn Gly His His Ser Asn Asp Val Ala Phe Asp Gly Thr Val Pro Leu
             20                  25                  30 atg gag aac aac att gtt aag aaa aca gac gac ggc tac gcc aat gga    385
Met Glu Asn Asn Ile Val Lys Lys Thr Asp Asp Gly Tyr Ala Asn Gly
         35                  40                  45 gga gga aag gcg tcg ttt atg aca tgg acg gcg cgt gac gct atc tac    433
Gly Gly Lys Ala Ser Phe Met Thr Trp Thr Ala Arg Asp Ala Ile Tyr
```

```
                50                  55                  60
gtg gcg aga gtc cat tgg ata ccg tgt gtg ttc gcg gtt gga gtt ctc     481
Val Ala Arg Val His Trp Ile Pro Cys Val Phe Ala Val Gly Val Leu
 65                  70                  75                  80 ttc ttc atg ggc gtc gag tat acg ctt caa atg att ccc gcg agg tct     529
Phe Phe Met Gly Val Glu Tyr Thr Leu Gln Met Ile Pro Ala Arg Ser
                     85                  90                  95 gag ccg ttc gat att ggg ttt gtg gtc acg cgc tct ctg aac cgc gtc     577
Glu Pro Phe Asp Ile Gly Phe Val Val Thr Arg Ser Leu Asn Arg Val
                100                 105                 110 ttg gca aat tca ccg gct ctt aac acc gtt tta gcc gca cta aac acg     625
Leu Ala Asn Ser Pro Ala Leu Asn Thr Val Leu Ala Ala Leu Asn Thr
            115                 120                 125 gtg ttc gta ggg atg caa act acg tat att gta tgg aca tgg ttg atg     673
Val Phe Val Gly Met Gln Thr Thr Tyr Ile Val Trp Thr Trp Leu Met
        130                 135                 140 gaa gga aga cca cgg gcc acc atc tcg gct tgc ttc atg ttt act tgt     721
Glu Gly Arg Pro Arg Ala Thr Ile Ser Ala Cys Phe Met Phe Thr Cys
145                 150                 155                 160 cgc gac tct acc cag ctt cct ctc cct cag gag ttt tta gga tca gga     769
Arg Asp Ser Thr Gln Leu Pro Leu Pro Gln Glu Phe Leu Gly Ser Gly
                165                 170                 175 gtc gat ttt ccg gtg gga aac gtc tca ttc ttc ctc ttc tac tcg ggt     817
Val Asp Phe Pro Val Gly Asn Val Ser Phe Phe Leu Phe Tyr Ser Gly
                180                 185                 190 cac gtc gcc ggt tcc atg ata gca tcc ttg gac atg agg aga atg cag     865
His Val Ala Gly Ser Met Ile Ala Ser Leu Asp Met Arg Arg Met Gln
            195                 200                 205 agg ttg aga cta gcg atg ctt ttt gac atc ctc aat gta cta caa tcc     913
Arg Leu Arg Leu Ala Met Leu Phe Asp Ile Leu Asn Val Leu Gln Ser
        210                 215                 220 atc agg ctg ctc ggg acg aga gga cat tac acc atc gat ctt gcg gtc     961
Ile Arg Leu Leu Gly Thr Arg Gly His Tyr Thr Ile Asp Leu Ala Val
225                 230                 235                 240 gga gtt ggc gct ggg att ctc ttt gac tcg ttg gcc ggg aag tac gaa    1009
Gly Val Gly Ala Gly Ile Leu Phe Asp Ser Leu Ala Gly Lys Tyr Glu
                245                 250                 255 gag atg atg agc aaa aga cac aat tta ggc aat ggt ttt agt ttg att    1057
Glu Met Met Ser Lys Arg His Asn Leu Gly Asn Gly Phe Ser Leu Ile
                260                 265                 270 tc                                                                 1059

<210> SEQ ID NO 6
<211> LENGTH: 272
<212> TYPE: PRT
<213> ORGANISM: Brassica juncea

<400> SEQUENCE: 6

Met Ser Thr Glu Thr Ser Val Pro Leu Arg Arg Ser Thr Ser Leu
  1               5                  10                  15

Asn Gly His His Ser Asn Asp Val Ala Phe Asp Gly Thr Val Pro Leu
                 20                  25                  30

Met Glu Asn Asn Ile Val Lys Lys Thr Asp Asp Gly Tyr Ala Asn Gly
             35                  40                  45

Gly Gly Lys Ala Ser Phe Met Thr Trp Thr Ala Arg Asp Ala Ile Tyr
         50                  55                  60

Val Ala Arg Val His Trp Ile Pro Cys Val Phe Ala Val Gly Val Leu
 65                  70                  75                  80
```

```
Phe Phe Met Gly Val Glu Tyr Thr Leu Gln Met Ile Pro Ala Arg Ser
                85                  90                  95
Glu Pro Phe Asp Ile Gly Phe Val Val Thr Arg Ser Leu Asn Arg Val
            100                 105                 110
Leu Ala Asn Ser Pro Ala Leu Asn Thr Val Leu Ala Ala Leu Asn Thr
        115                 120                 125
Val Phe Val Gly Met Gln Thr Thr Tyr Ile Val Trp Thr Trp Leu Met
130                 135                 140
Glu Gly Arg Pro Arg Ala Thr Ile Ser Ala Cys Phe Met Phe Thr Cys
145                 150                 155                 160
Arg Asp Ser Thr Gln Leu Pro Leu Pro Gln Glu Phe Leu Gly Ser Gly
                165                 170                 175
Val Asp Phe Pro Val Gly Asn Val Ser Phe Phe Leu Phe Tyr Ser Gly
            180                 185                 190
His Val Ala Gly Ser Met Ile Ala Ser Leu Asp Met Arg Arg Met Gln
        195                 200                 205
Arg Leu Arg Leu Ala Met Leu Phe Asp Ile Leu Asn Val Leu Gln Ser
    210                 215                 220
Ile Arg Leu Leu Gly Thr Arg Gly His Tyr Thr Ile Asp Leu Ala Val
225                 230                 235                 240
Gly Val Gly Ala Gly Ile Leu Phe Asp Ser Leu Ala Gly Lys Tyr Glu
                245                 250                 255
Glu Met Met Ser Lys Arg His Asn Leu Gly Asn Gly Phe Ser Leu Ile
            260                 265                 270

<210> SEQ ID NO 7
<211> LENGTH: 1089
<212> TYPE: DNA
<213> ORGANISM: Brassica juncea
<220> FEATURE:
<221> NAME/KEY: CDS
<222> LOCATION: (173)..(979)

<400> SEQUENCE: 7
agaaaagaat aacgaggcaa aagacttgcg taaacgtagc tctagaacct catactcatc    60
gttttcgtat gaattttttgt agaccaaaca atcttccttc cacagttcac aaaatataaa   120
acaatacctc cttcgagatc tctgcctctt acataaccca tatctcacgc tt atg tca   178
                                                          Met Ser
                                                            1 act gaa act ggc gtc cct ctc cgt cgc aga tct aac tct ctt aac gga    226
Thr Glu Thr Gly Val Pro Leu Arg Arg Arg Ser Asn Ser Leu Asn Gly
        5                   10                  15 cat cac act aac ggc gtc gcc tct gac gga aca aac gtc cca tta atg    274
His His Thr Asn Gly Val Ala Ser Asp Gly Thr Asn Val Pro Leu Met
    20                  25                  30 gag aag gcg tcg ttt atg aca tgg acg gcg cgt gac gct atc tac gtg    322
Glu Lys Ala Ser Phe Met Thr Trp Thr Ala Arg Asp Ala Ile Tyr Val
35                  40                  45                  50 gcg aga gtc cat tgg ata ccg tgt gtg ttc gcg gtc gga gtt ctg ttc    370
Ala Arg Val His Trp Ile Pro Cys Val Phe Ala Val Gly Val Leu Phe
                55                  60                  65 ttc atg ggc gtc gag tat acg ctt cag atg att ccc gcg agg tct gag    418
Phe Met Gly Val Glu Tyr Thr Leu Gln Met Ile Pro Ala Arg Ser Glu
            70                  75                  80 ccg ttc gat att ggg ttc gtg gcc acg cgc tct ctg aat cgc gtc ttg    466
Pro Phe Asp Ile Gly Phe Val Ala Thr Arg Ser Leu Asn Arg Val Leu
        85                  90                  95
```

| | | |
|---|---|---|
| gca gat tca ccg gat ctt aac acc gtt tta gct gca cta aac acg gtt<br>Ala Asp Ser Pro Asp Leu Asn Thr Val Leu Ala Ala Leu Asn Thr Val<br>100                      105                      110 | | 514 |
| ttc gta ggg atg caa act acg tat att gta tgg aca tgg ttg atg gaa<br>Phe Val Gly Met Gln Thr Thr Tyr Ile Val Trp Thr Trp Leu Met Glu<br>115                      120                      125                      130 | | 562 |
| gga aga cca cgg gcc acc atc tcg gct tgc ttc atg ttt act tgt cgc<br>Gly Arg Pro Arg Ala Thr Ile Ser Ala Cys Phe Met Phe Thr Cys Arg<br>                135                      140                      145 | | 610 |
| ggt att ctt ggt tac tct act cag ctc cct ctc cct cag gag ttt tta<br>Gly Ile Leu Gly Tyr Ser Thr Gln Leu Pro Leu Pro Gln Glu Phe Leu<br>150                      155                      160 | | 658 |
| gga tca gga gtc gat ttt ccg gtg gga aac gtc tca ttc ttc ctc ttc<br>Gly Ser Gly Val Asp Phe Pro Val Gly Asn Val Ser Phe Phe Leu Phe<br>                165                      170                      175 | | 706 |
| tac tcg ggt cac gtc gcc ggt tcc atg ata gca tcc ttg gac atg agg<br>Tyr Ser Gly His Val Ala Gly Ser Met Ile Ala Ser Leu Asp Met Arg<br>180                      185                      190 | | 754 |
| aga atg cag agg ttg aga cta gcg atg ctt ttt gac atc ctc aat gta<br>Arg Met Gln Arg Leu Arg Leu Ala Met Leu Phe Asp Ile Leu Asn Val<br>195                      200                      205                      210 | | 802 |
| cta caa tcc atc agg ctg ctc ggg acg aga gga cat tac acc atc gat<br>Leu Gln Ser Ile Arg Leu Leu Gly Thr Arg Gly His Tyr Thr Ile Asp<br>                215                      220                      225 | | 850 |
| ctt gcg gtc gga gtt ggc gct ggg att ctc ttt gac tcg ttg gcc ggg<br>Leu Ala Val Gly Val Gly Ala Gly Ile Leu Phe Asp Ser Leu Ala Gly<br>                     230                      235                      240 | | 898 |
| aag tac gaa gag atg atg agc aaa aga cac aat tta ggc aat ggt ttt<br>Lys Tyr Glu Glu Met Met Ser Lys Arg His Asn Leu Gly Asn Gly Phe<br>                245                      250                      255 | | 946 |
| agt ttg att tct aaa gac tcg cta gtc aat taa ttttgtttaa ttctttga<br>Ser Leu Ile Ser Lys Asp Ser Leu Val Asn<br>260                      265 | | 999 |
| aatgtttagt tgaacttgaa catattaaat ttaattgatg tccaatgaat taaatttatt | | 1059 |
| ttctttccga tgattctgac tgaaaggat | | 1089 |

```
<210> SEQ ID NO 8
<211> LENGTH: 268
<212> TYPE: PRT
<213> ORGANISM: Brassica juncea

<400> SEQUENCE: 8
```

Met Ser Thr Glu Thr Gly Val Pro Leu Arg Arg Arg Ser Asn Ser Leu
1               5                   10                  15

Asn Gly His His Thr Asn Gly Val Ala Ser Asp Gly Thr Asn Val Pro
            20                  25                  30

Leu Met Glu Lys Ala Ser Phe Met Thr Trp Thr Ala Arg Asp Ala Ile
        35                  40                  45

Tyr Val Ala Arg Val His Trp Ile Pro Cys Val Phe Ala Val Gly Val
    50                  55                  60

Leu Phe Phe Met Gly Val Glu Tyr Thr Leu Gln Met Ile Pro Ala Arg
65                  70                  75                  80

Ser Glu Pro Phe Asp Ile Gly Phe Val Ala Thr Arg Ser Leu Asn Arg
                85                  90                  95

Val Leu Ala Asp Ser Pro Asp Leu Asn Thr Val Leu Ala Ala Leu Asn
            100                 105                 110

Thr Val Phe Val Gly Met Gln Thr Thr Tyr Ile Val Trp Thr Trp Leu
        115                 120                 125

```
Met Glu Gly Arg Pro Arg Ala Thr Ile Ser Ala Cys Phe Met Phe Thr
    130                 135                 140

Cys Arg Gly Ile Leu Gly Tyr Ser Thr Gln Leu Pro Leu Pro Gln Glu
145                 150                 155                 160

Phe Leu Gly Ser Gly Val Asp Phe Pro Val Gly Asn Val Ser Phe Phe
                165                 170                 175

Leu Phe Tyr Ser Gly His Val Ala Gly Ser Met Ile Ala Ser Leu Asp
                180                 185                 190

Met Arg Arg Met Gln Arg Leu Arg Leu Ala Met Leu Phe Asp Ile Leu
            195                 200                 205

Asn Val Leu Gln Ser Ile Arg Leu Leu Gly Thr Arg Gly His Tyr Thr
    210                 215                 220

Ile Asp Leu Ala Val Gly Val Gly Ala Gly Ile Leu Phe Asp Ser Leu
225                 230                 235                 240

Ala Gly Lys Tyr Glu Glu Met Met Ser Lys Arg His Asn Leu Gly Asn
                245                 250                 255

Gly Phe Ser Leu Ile Ser Lys Asp Ser Leu Val Asn
                260                 265
```

```
<210> SEQ ID NO 9
<211> LENGTH: 953
<212> TYPE: DNA
<213> ORGANISM: Brassica juncea
<220> FEATURE:
<221> NAME/KEY: CDS
<222> LOCATION: (53)..(922)

<400> SEQUENCE: 9
acccatctct ctaagcctct caaaacgttc ttctccgtta aatctaacgg tc atg tca      58
                                                        Met Ser
                                                          1 act aca aca atc gtc cct ctc cgt cgc act tct aac tct ctc aat gaa     106
Thr Thr Thr Ile Val Pro Leu Arg Arg Thr Ser Asn Ser Leu Asn Glu
        5                  10                  15 tac cac act aac gca gtc gcc ttt gac gga atc gtc ggg tca gca agt     154
Tyr His Thr Asn Ala Val Ala Phe Asp Gly Ile Val Gly Ser Ala Ser
 20                  25                  30 act agc caa atg gag gag att gtt acg caa acc gac gac tgc tac gcc     202
Thr Ser Gln Met Glu Glu Ile Val Thr Gln Thr Asp Asp Cys Tyr Ala
 35                  40                  45                  50 aac ccc aac gga gat gga ggg aga agc aag gtg tcg tta atg acg tgg     250
Asn Pro Asn Gly Asp Gly Gly Arg Ser Lys Val Ser Leu Met Thr Trp
                 55                  60                  65 agg atg tgc aat cct gtc cac gtg gtg aga gtc cat tgg ata ccg tgt     298
Arg Met Cys Asn Pro Val His Val Val Arg Val His Trp Ile Pro Cys
             70                  75                  80 ttg tta gcg gta gga gtt ctg ttc ttc acg tgc gta gag gag tac atg     346
Leu Leu Ala Val Gly Val Leu Phe Phe Thr Cys Val Glu Glu Tyr Met
         85                  90                  95 ctc cag atg att ccg gcg agt tct gag ccg ttc gat att ggt ttt gtg     394
Leu Gln Met Ile Pro Ala Ser Ser Glu Pro Phe Asp Ile Gly Phe Val
     100                 105                 110 gcg acg ggc tct ctg tat cgc ctc ttg gct tct tca ccg gat ctt aat     442
Ala Thr Gly Ser Leu Tyr Arg Leu Leu Ala Ser Ser Pro Asp Leu Asn
115                 120                 125                 130 acc gtt tta gct gct ctc aac acg gtg ttt gta ggg atg caa acg acg     490
Thr Val Leu Ala Ala Leu Asn Thr Val Phe Val Gly Met Gln Thr Thr
                135                 140                 145
```

| | | |
|---|---|---|
| tat att gta tgg aca tgg ttg atg gaa gga cga cca cga gcg acc atc<br>Tyr Ile Val Trp Thr Trp Leu Met Glu Gly Arg Pro Arg Ala Thr Ile<br>            150                 155                 160 | | 538 |
| tcg gct tgc ttt atg ttt act tgc cgt ggc att ctg ggt tac tct act<br>Ser Ala Cys Phe Met Phe Thr Cys Arg Gly Ile Leu Gly Tyr Ser Thr<br>        165                 170                 175 | | 586 |
| cag ctc cct ctt cct cag gat ttt cta gga tca ggg gta gat ttt ccg<br>Gln Leu Pro Leu Pro Gln Asp Phe Leu Gly Ser Gly Val Asp Phe Pro<br>    180                 185                 190 | | 634 |
| gta gga aac gtc tcg ttc ttc ctc ttc tac tca ggc cat gtc gca ggg<br>Val Gly Asn Val Ser Phe Phe Leu Phe Tyr Ser Gly His Val Ala Gly<br>195                 200                 205                 210 | | 682 |
| tcg acg ata gca tcc ttg gat atg agg aga atg aag agg ttg aga ctt<br>Ser Thr Ile Ala Ser Leu Asp Met Arg Arg Met Lys Arg Leu Arg Leu<br>                215                 220                 225 | | 730 |
| gcc ttg ctt ttt gac atc ctc aat gta tta caa tcg atc agg ctt ctc<br>Ala Leu Leu Phe Asp Ile Leu Asn Val Leu Gln Ser Ile Arg Leu Leu<br>            230                 235                 240 | | 778 |
| ggg acg aga gga caa tac acg atc gat ctc gct gtc gga gtt ggc gct<br>Gly Thr Arg Gly Gln Tyr Thr Ile Asp Leu Ala Val Gly Val Gly Ala<br>        245                 250                 255 | | 826 |
| ggg gtt ctc ttt gac tca ctg gct gga aaa tac gaa gag atg atg agc<br>Gly Val Leu Phe Asp Ser Leu Ala Gly Lys Tyr Glu Glu Met Met Ser<br>    260                 265                 270 | | 874 |
| aag aga cac aat gta ggc aat ggt ttt agt tta att tcg act cgc tag<br>Lys Arg His Asn Val Gly Asn Gly Phe Ser Leu Ile Ser Thr Arg<br>275                 280                 285 | | 922 |
| ttattaattt ttgtttttttt ctttatgttt t | | 953 |

<210> SEQ ID NO 10
<211> LENGTH: 289
<212> TYPE: PRT
<213> ORGANISM: Brassica juncea

<400> SEQUENCE: 10

Met Ser Thr Thr Thr Ile Val Pro Leu Arg Arg Thr Ser Asn Ser Leu
1               5                   10                  15

Asn Glu Tyr His Thr Asn Ala Val Ala Phe Asp Gly Ile Val Gly Ser
                20                  25                  30

Ala Ser Thr Ser Gln Met Glu Glu Ile Val Thr Gln Thr Asp Asp Cys
            35                  40                  45

Tyr Ala Asn Pro Asn Gly Asp Gly Gly Arg Ser Lys Val Ser Leu Met
        50                  55                  60

Thr Trp Arg Met Cys Asn Pro Val His Val Val Arg Val His Trp Ile
65                  70                  75                  80

Pro Cys Leu Leu Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Val Trp Thr Trp Leu Met Glu Gly Arg Pro Arg Ala
145                 150                 155                 160

Thr Ile Ser Ala Cys Phe Met Phe Thr Cys Arg Gly Ile Leu Gly Tyr
                165                 170                 175

```
Ser Thr Gln Leu Pro Leu Pro Gln Asp Phe Leu Gly Ser Gly Val Asp
            180                 185                 190

Phe Pro Val Gly Asn Val Ser Phe Leu Phe Tyr Ser Gly His Val
            195                 200                 205

Ala Gly Ser Thr Ile Ala Ser Leu Asp Met Arg Arg Met Lys Arg Leu
            210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                    245                 250                 255

Gly Ala Gly Val Leu Phe Asp Ser Leu Ala Gly Lys Tyr Glu Glu Met
            260                 265                 270

Met Ser Lys Arg His Asn Val Gly Asn Gly Phe Ser Leu Ile Ser Thr
            275                 280                 285

Arg

<210> SEQ ID NO 11
<211> LENGTH: 1040
<212> TYPE: DNA
<213> ORGANISM: Brassica juncea
<220> FEATURE:
<221> NAME/KEY: CDS
<222> LOCATION: (70)..(939)

<400> SEQUENCE: 11
ataatatctc ttatatattc catttctcta agcctctcga aatgttcttc tccgttaaat      60 ctaacggcc atg tca act aca aca atc gtc cct ctc cgt cgg agt tct aac    111
           Met Ser Thr Thr Thr Ile Val Pro Leu Arg Arg Ser Ser Asn
             1               5                  10 tct ctc aat gaa tac cac act aac gca gtc gcc ttt gac gga atc gtc    159
Ser Leu Asn Glu Tyr His Thr Asn Ala Val Ala Phe Asp Gly Ile Val
 15              20                  25                  30 ggg tca aca agt act agc caa atg gag gag att gtt acg caa atg gac    207
Gly Ser Thr Ser Thr Ser Gln Met Glu Glu Ile Val Thr Gln Met Asp
                 35                  40                  45 gaa ggc tac gcc aac ccc aac gga gat gga ggg aga agc aag gtg tcg    255
Glu Gly Tyr Ala Asn Pro Asn Gly Asp Gly Gly Arg Ser Lys Val Ser
         50                  55                  60 ttc atg acg tgg agg atg tgc agt gct gtc cac gtg gtg aga gtc cac    303
Phe Met Thr Trp Arg Met Cys Ser Ala Val His Val Val Arg Val His
 65                  70                  75 tgg ata ccg tgt ttg tta gcg gta gga gtt ctg ttc ttc acg ggg gtg    351
Trp Ile Pro Cys Leu Leu Ala Val Gly Val Leu Phe Phe Thr Gly Val
 80                  85                  90 gag gag tac atg ctc cag atg att ccc ccg agt tct gag ccg ttc gat    399
Glu Glu Tyr Met Leu Gln Met Ile Pro Pro Ser Ser Glu Pro Phe Asp
 95                 100                 105                 110 att ggt ttt gtg gcg acg cgc tct ctc tat cgc ctc ttg gct tct tca    447
Ile Gly Phe Val Ala Thr Arg Ser Leu Tyr Arg Leu Leu Ala Ser Ser
                115                 120                 125 ccg gat ctc aac acc gtt tta gcc gct ctc aac acg gtg ttc gta ggg    495
Pro Asp Leu Asn Thr Val Leu Ala Ala Leu Asn Thr Val Phe Val Gly
        130                 135                 140 atg caa acg acg tat att gta tgg aca tgg ttg atg gaa gga cga cca    543
Met Gln Thr Thr Tyr Ile Val Trp Thr Trp Leu Met Glu Gly Arg Pro
    145                 150                 155 cga gcg acc atc tcg gct tgc ttt atg ttt aca tgt cgt ggc att ctt    591
Arg Ala Thr Ile Ser Ala Cys Phe Met Phe Thr Cys Arg Gly Ile Leu
160                 165                 170
```

```
ggt tac tct act cag ctc cct ctt cct cag gat ttt cta gga tca ggg      639
Gly Tyr Ser Thr Gln Leu Pro Leu Pro Gln Asp Phe Leu Gly Ser Gly
175                 180                 185                 190 gta gac ttt cct gta gga aac gtc tcc ttc ctc ttc tac tca ggc          687
Val Asp Phe Pro Val Gly Asn Val Ser Phe Leu Phe Tyr Ser Gly
                195                 200                 205 cat gtg gca ggg tcg acg ata gca tcc ttg gac atg agg aga atg aag      735
His Val Ala Gly Ser Thr Ile Ala Ser Leu Asp Met Arg Arg Met Lys
                210                 215                 220 agg ttg aga cta gcc ttg ctt ttt gac atc ctc aat gta tta caa tcg      783
Arg Leu Arg Leu Ala Leu Leu Phe Asp Ile Leu Asn Val Leu Gln Ser
            225                 230                 235 atc agg ctt ctc ggg acg aga gga caa tac acg atc gat ctc gct gtc      831
Ile Arg Leu Leu Gly Thr Arg Gly Gln Tyr Thr Ile Asp Leu Ala Val
        240                 245                 250 gga gtt ggc gct ggg gtt ctc ttt gac tca ctg gct gga aaa tac gaa      879
Gly Val Gly Ala Gly Val Leu Phe Asp Ser Leu Ala Gly Lys Tyr Glu
255                 260                 265                 270 gag atg atg agc aag aga cac aat gta ggc aat ggt ttt agt ttg att      927
Glu Met Met Ser Lys Arg His Asn Val Gly Asn Gly Phe Ser Leu Ile
                275                 280                 285 tcg tct cgc tag ttattaattt tgttttttt tttatgtttt tagcctggac          979
Ser Ser Arg atatttaatt tagttgaaat ctaatgactt aaatttactt tctttcaaaa tgctctaact  1039
g                                                                 1040

<210> SEQ ID NO 12
<211> LENGTH: 289
<212> TYPE: PRT
<213> ORGANISM: Brassica juncea

<400> SEQUENCE: 12

Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
                20                  25                  30

Thr Ser Thr Ser Gln Met Glu Glu Ile Val Thr Gln Met Asp Glu Gly
            35                  40                  45

Tyr Ala Asn Pro Asn Gly Asp Gly Gly Arg Ser Lys Val Ser Phe Met
        50                  55                  60

Thr Trp Arg Met Cys Ser Ala Val His Val Val Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Pro Ser Ser Glu Pro Phe Asp Ile Gly
                100                 105                 110

Phe Val Ala Thr Arg Ser Leu Tyr Arg Leu Leu Ala Ser Ser Pro Asp
            115                 120                 125

Leu Asn Thr Val Leu Ala Ala Leu Asn Thr Val Phe Val Gly Met Gln
        130                 135                 140

Thr Thr Tyr Ile Val Trp Thr Trp Leu Met Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
                180                 185                 190
```

```
Phe Pro Val Gly Asn Val Ser Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
                260                 265                 270

Met Ser Lys Arg His Asn Val Gly Asn Gly Phe Ser Leu Ile Ser Ser
                275                 280                 285

Arg

<210> SEQ ID NO 13
<211> LENGTH: 1014
<212> TYPE: DNA
<213> ORGANISM: Brassica juncea
<220> FEATURE:
<221> NAME/KEY: CDS
<222> LOCATION: (23)..(730)

<400> SEQUENCE: 13
aaaaaaaaca aggaataata aa atg tct caa atg gac att tct acg aga act         52
                         Met Ser Gln Met Asp Ile Ser Thr Arg Thr
                           1               5                  10 gag gaa gga gga tgg aga agc aag cct tcg ttc atg acg tgg aga gcg         100
Glu Glu Gly Gly Trp Arg Ser Lys Pro Ser Phe Met Thr Trp Arg Ala
                 15                  20                  25 cgc gac gtt gtc tac gtg atg aga cac cat tgg ata ccg tgt ctg ttc         148
Arg Asp Val Val Tyr Val Met Arg His His Trp Ile Pro Cys Leu Phe
             30                  35                  40 gcg gcc gga ttc ttg ttc gtc gta agc gtg gag tcc tcg atc aag atg         196
Ala Ala Gly Phe Leu Phe Val Val Ser Val Glu Ser Ser Ile Lys Met
         45                  50                  55 gtt tcc gag agt tct cca ccg ttc gat att ggg ttt gtg gcc acg gag         244
Val Ser Glu Ser Ser Pro Pro Phe Asp Ile Gly Phe Val Ala Thr Glu
 60                  65                  70 tct ctg cat cat atc ttg gct tct tca ccg gat ctg aac acc ggt ttg         292
Ser Leu His His Ile Leu Ala Ser Ser Pro Asp Leu Asn Thr Gly Leu
 75                  80                  85                  90 gcc gct cta aac tcg gtg tta gga gtg atg caa gta tcg tat att gca         340
Ala Ala Leu Asn Ser Val Leu Gly Val Met Gln Val Ser Tyr Ile Ala
                 95                 100                 105 tgg aca tgg tta ata gaa gga cgg cca cga gcc acc atc acg gct tta         388
Trp Thr Trp Leu Ile Glu Gly Arg Pro Arg Ala Thr Ile Thr Ala Leu
             110                 115                 120 ttc ctc ttc act tgt cgc ggc gtt ctc ggt tac tgt acg cag ctc cct         436
Phe Leu Phe Thr Cys Arg Gly Val Leu Gly Tyr Cys Thr Gln Leu Pro
         125                 130                 135 ctt tca aag gag tat cta gga tca gca atc gat ttc ccg cta gga aac         484
Leu Ser Lys Glu Tyr Leu Gly Ser Ala Ile Asp Phe Pro Leu Gly Asn
     140                 145                 150 ctc tcg ttc ttc tat ttt ttc tcg ggt cac gtg gca ggc acg acc atc         532
Leu Ser Phe Phe Tyr Phe Phe Ser Gly His Val Ala Gly Thr Thr Ile
155                 160                 165                 170 gca tct ttg gac atg agg aga atg cag agg ttg aga ctt gcg atg gtt         580
Ala Ser Leu Asp Met Arg Arg Met Gln Arg Leu Arg Leu Ala Met Val
                 175                 180                 185
```

```
ttt gac atc ctc aat gta tta cag tcg atc agg ctg ctt gcg acg aga    628
Phe Asp Ile Leu Asn Val Leu Gln Ser Ile Arg Leu Leu Ala Thr Arg
            190                 195                 200 gga cac tac acg atc gat ctc gca ggt gga gtt gcc gcc gcg att ctc    676
Gly His Tyr Thr Ile Asp Leu Ala Gly Gly Val Ala Ala Ala Ile Leu
            205                 210                 215 ttt gac tca ttg gcc ggc aag tac gaa gca aat aca aga aag agg caa    724
Phe Asp Ser Leu Ala Gly Lys Tyr Glu Ala Asn Thr Arg Lys Arg Gln
220                 225                 230 ttg tag gaacaggttt cagcttgatt accaaaagac ttcaaagatt tcattcaaca     780
Leu
235 tgtttagttg ctgttgaatt aagtctactg tggttcggca attattctcc ccatgagcca  840 gtggcttgga cttcttcgac cctaatgttc atggtcagac tgtatatgtt gtttatttct  900 cattttttca ttcaactccg caatttgtga tatgggtttg gttaacacta gttggttcag  960 ttgttttcaa ttggttttac tctgaaagtt ataaacgttt gtaataccca gatt        1014
```

<210> SEQ ID NO 14
<211> LENGTH: 235
<212> TYPE: PRT
<213> ORGANISM: Brassica juncea

<400> SEQUENCE: 14

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
                20                  25                  30

Met Arg His His Trp Ile Pro Cys Leu Phe Ala Ala Gly Phe Leu Phe
            35                  40                  45

Val Val Ser Val Glu Ser Ser Ile Lys Met Val Ser Glu Ser Ser Pro
        50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
                100                 105                 110

Gly Arg Pro Arg Ala Thr Ile Thr Ala Leu Phe Leu Phe Thr Cys Arg
            115                 120                 125

Gly Val Leu Gly Tyr Cys Thr Gln Leu Pro Leu Ser Lys Glu Tyr Leu
        130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

US 9,873,886 B2

BRASSICA ROD1 GENE SEQUENCES AND USES THEREOF

CROSS REFERENCE TO RELATED APPLICATIONS

This application claims the benefit of U.S. Provisional Application Ser. No. 61/669,370, filed Jul. 9, 2012 and European Patent Application Serial No. 12175303.2, filed Jul. 6, 2012, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS12-2011_ST25sequence listing," created on Jul. 11, 2013 and having a size of 48 kilobytes and is filed concurrently with the specification. The sequence listing contained in this ASCII formatted document is part of the specification and is herein incorporated by reference in its entirety.

FIELD OF THE INVENTION

The invention relates to the field of agronomy. Methods and means are provided to modulate fatty acid composition in *Brassica juncea*, such as to increase levels of unsaturated fatty acids in *Brassica juncea* by modulation of expression of ROD1 genes in various manners, including provision of knock-out ROD1 alleles or providing inhibitory RNAs to the ROD1 genes.

BACKGROUND OF THE INVENTION

Many plant species store triacylglycerols (TAGs) in their seeds as a carbon reserve. These TAGs are the major source of energy and carbon material that supports seedling development during the early stages of plant life. Vegetable oils from soybean (*Glycine max*), Brassica (*Brassica napus* or *B. rapa*), sunflower (*Helianthus annuus*) and many other oilseed crops are also an important source of oil for the human diet or industrial applications including, but not limited to biofuels, biolubricants, nylon precursors, and detergent feedstocks. The degree and/or amount of polyunsaturated fatty acids of vegetable oils are characteristic and determinative properties with respect to oil uses in food or non-food industries. More specifically, the characteristic properties and utilities of vegetable oils are largely determined by their fatty acyl compositions in TAG.

Major vegetable oils are comprised primarily of palmitic (16:0), stearic (18:0), oleic (18:1cis $\Delta^9$), linoleic (18:2cis $\Delta^{9,12}$), and α-linolenic (18:3cis $\Delta^{9,12,15}$ or C18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a monounsaturated fatty acid, while linoleic and linolenic acids are referred to as polyunsaturated fatty acids. Modifications of the fatty acid compositions have been sought after for at least a century in order to provide optimal oil products for human nutrition and chemical (e.g., oleochemical) uses (Gunstone, 1998, Prog Lipid Res 37:277; Broun et al., 1999, Annu Rev Nutr 19:107; Jaworski et al, 2003, Curr Opin Plant Biol 6:178). In particular, the polyunsaturated fatty acids (18:2 and 18:3) have received considerable attention because they are major factors that affect nutritional value and oil stability. However, while these two fatty acids provide essential nutrients for humans and animals, they increase oil instability because they comprise multiple double bonds that may be easily oxidized during processing and storage.

The desaturation of 18:1 into 18:2 is a critical step for synthesizing polyunsaturated fatty acids. During storage lipid biosynthesis, this reaction is known to be catalyzed by the fatty acid desaturase, FAD2, a membrane-bound enzyme located on the endoplasmic reticulum (ER) (Browse and Somerville, 1991, Annu Rev Plant Physiol Plant Mol Biol 42:467). The FAD2 substrate 18:1 must be esterified on the sn-2 position of phosphatidylcholine (PC) (Miguel and Browse, 1992, J Biol Chem 267:1502; Okuley et al., 1994, Plant Cell 6:147), which is the major membrane phospholipid of plant cells. Not surprisingly, therefore, down-regulation of FAD2 (and FAD3) genes has become a preferred strategy for avoiding the need to hydrogenate vegetable oils and the concomitant production of undesirable trans fatty acids. For example, soybean has both seed-specific and constitutive FAD2 desaturases, so that gene silencing of the seed-specific isoform has allowed the production of high-oleate cultivars (>88% 18:1 in the oil) in which membrane unsaturation and plant performance are largely unaffected. Significantly, however, such FAD2 gene-silencing strategies are substantially limited because, for example, canola and other oilseed plants have only constitutive FAD2 enzymes. Therefore, in canola and other such constitutive FAD2 crops, silencing or down-regulation of FAD2 not only alters the fatty acid composition of the storage triacylglycerol (TAG) in seeds, but also of the cellular membranes, which severely compromises growth and yield of the plant. For example, the defective FAD2 in the *Arabidopsis* mutant fad2 alters fatty acid compositions of seeds as well as vegetable tissues, and severely compromises plant growth (Browse and Somerville, supra). FAD2 mutations and silencing that produce the highest 18:1 levels in the oil also reduce membrane unsaturation in vegetative and seed tissues, resulting in plants that germinate and grow poorly. As a result, only partial downregulation of FAD2 expression is possible, producing approximately 70-75% 18:1 in the oil of commercial cultivars such as Nexera/Natreon (Dow Agro-Sciences) and Clear Valley 75 (Cargill). Lu et al (2009, Proc Natl Acad Sci USA 106:18837) and WO2009/111587 describe the identification of phosphatidylcholine:diacylglycerol cholinephosphotransferase (PDCT) from *Arabidopsis*, which is endoced by the ROD1 gene, which is involved in the transfer of 18:1 into phosphatidylcholine for desaturation and also for the reverse transfer of 18:2 and 18:3 into the triacylglycerol synthesis pathway. The PDCT enzyme catalyzes transfer of 18:2 and 18:3 into the triacylglycerol synthesis pathway. Seeds of an *Arabidopsis* rod1 mutant have a decrease in 18:2 and 18:3 polyunsaturated fatty acids and a concomitant increase in 18:1 relative to wild-type, whereas there is no effect on the fatty acid compositions of leaf or root tissues. identified in *Arabidopsis*. WO2009/111587 further describes ROD1 homologs from *Brassica napus, Brassica rapa*, and *Brassica oleracea*.

In order to use the ROD1 gene to increase 18:1 levels and reduce 18:2 and 18:3 levels in *Brassica juncea*, a need remains for knowing all ROD1 gene sequences and the functionality of the encoded proteins in the *Brassica juncea* genome. The isolation of mutant alleles corresponding to rod1 in *Brassica juncea* may be complicated by the amphidiploidy and the consequent functional redundancy of the corresponding genes.

Thus, the prior art is deficient in teaching the ROD1 gene sequences and the number of ROD1 genes in *Brassica juncea*, and which of the ROD1 genes encode a functional protein or need to be inactivated in order to increase the levels of 18:1 in *Brassica juncea*. As described hereinafter, this problem has been solved, allowing to modulate expression of PDCT with the aim to modulate the 18:1 levels in *Brassica juncea*, as will become apparent from the different embodiments and the claims.

SUMMARY OF THE INVENTION

It is a first embodiment of the invention to provide a *Brassica juncea* plant or plant cell, part, seed or progeny thereof, comprising at least one ROD1 gene, characterized in that at least one ROD1 gene is an inactivated or a knock-out rod1 gene. In a further embodiment, said plant comprises two knock-out rod1 genes. In yet a further embodiment, said knock-out gene is a knock-out allele of the ROD1 gene encoding a protein having at least 90% sequence identity to SEQ ID No. 2 or SEQ ID No. 4. In a further embodiment, said *Brassica juncea* plant is homozygous for said knock-out rod1 gene.

In a further embodiment, a transgenic *Brassica juncea* plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells. In another embodiment, said RNA molecule is inhibitory to a ROD1 gene encoding a protein having at least 90% sequence identity to SEQ ID No. 2 or SEQ ID No. 4.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in *Brassica juncea* seed oil, comprising modulating the expression of a ROD1 gene. In yet another embodiment, a method is provided for increasing the C18:1 levels in *Brassica juncea* seed oil, comprising the steps of introducing or providing a chimeric gene to a *Brassica juncea* plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

In again another embodiment, a method is provided for increasing the C18:1 levels in seed oil, comprising the steps of treating seeds or plant material with a mutagenic chemical substance or with ionizing radiation; identifying plants with a mutated ROD1 gene, wherein the ROD1 gene, prior to being mutated, encodes a polypeptide having at least 90% sequence identity to SEQ ID No. 2 or to SEQ ID No. 4; and selecting a plant with an increased level of C18:1 in the seeds compared to a plant in which the ROD1 gene is not mutated.

In a further embodiment, a method is provided for obtaining a *Brassica juncea* plant with increased levels of C18:1 in the seeds comprising the step of introducing a knock-out allele of a ROD1 gene in said *Brassica juncea* plant, and selecting said *Brassica juncea* plant with increased levels of C18:1 levels in the seeds for the presence of said knock-out allele of a ROD1 gene by analyzing genomic DNA from said plant for the presence of at least one molecular marker, wherein said at least one molecular marker is linked to said knock-out allele of a ROD1 gene.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Yet another embodiment provides a kit for the detection of a knock-out allele of a ROD1 gene in *Brassica juncea* DNA samples, wherein said kit comprises one or more PCR primer pairs, which are able to amplify a DNA marker linked to said knock-out allele of a ROD1 gene.

In a further embodiment, a method is provided for determining the zygosity status of a mutant ROD1 allele in a *Brassica juncea* plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides a method for transferring at least one knock-out ROD1 allele from one *Brassica juncea* plant to another *Brassica juncea* plant comprising the steps of: identifying a first *Brassica juncea* plant comprising at least one knock-out ROD1 allele; crossing the first *Brassica juncea* plant with a second *Brassica juncea* plant not comprising the at least one knock-out ROD1 allele and collecting F1 hybrid seeds from the cross; optionally, identifying F1 *Brassica juncea* plants comprising the at least one knock-out ROD1 allele; backcrossing F1 *Brassica juncea* plants comprising the at least one knock-out ROD1 allele with the second plant not comprising the at least one knock-out ROD1 allele for at least one generation (x) and collecting BCx seeds from the crosses; identifying in every generation BCx *Brassica juncea* plants comprising the at least one knock-out ROD1 allele by analyzing genomic DNA of said BCx plants for the presence of at least one molecular marker, wherein the at least one molecular marker is linked to said knock-out ROD1 allele.

Another embodiment provides a chimeric gene comprising the following operably linked elements: a plant-expressible promoter; a DNA region, which when transcribed yields an RNA molecule inhibitory to at least one ROD1 gene, said ROD1 gene encoding a protein having at least 90% sequence identity to SEQ ID No. 2 or SEQ ID No. 4; and optionally a transcription termination and polyadenylation region functional in plant cells.

In again another embodiment, a knock-out allele of an ROD1 gene is provided, wherein the knock-out ROD1 allele is a mutated version of the native ROD1 gene selected from the group consisting of: a nucleic acid molecule which comprises at least 90% sequence identity to SEQ ID No. 1 or SEQ ID No. 3; or a nucleic acid molecule encoding an amino acid sequence comprising at least 90% sequence identity to SEQ ID No. 2 or SEQ ID No. 4, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

In a further embodiment, a method is provided for producing oil, comprising harvesting seeds from the plants according to the invention, i.e. *Brassica juncea* plants comprising an inactivated or a knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the *Brassica juncea* plant or a part thereof according to the invention, and preparing the food, feed or industrial product from the plant or part thereof.

GENERAL DEFINITIONS

A "ROD1 gene" or "ROD1 allele", as used herein, is a gene or allele comprising a sequence having at least 60% sequence identity to the coding sequence of the ROD1 gene of *Arabidopsis thaliana*, as described in WO2009/111587.

A ROD1 gene or ROD1 allele can, but does not need to encode a functional ROD1 protein. Functionality of the ROD1 protein can be tested, for example, in yeast as described in example 4 or as described by Lu et al. (2009) Proc Natl Acad Sci USA 106:18839.

A "knock-out rod1 gene" or "knock-out rod1 allele" as used herein is a rod1 gene or a rod1 allele which encodes no functional ROD1 protein, or which encodes a ROD1 protein with reduced activity. Said "knock-out rod1 gene" can be a full knock-out rod1 gene, encoding no functional ROD1 protein, or can be a partial knock-out rod1 gene, encoding a ROD1 protein with reduced activity. Said "knock-out rod1 gene" or "knock-out rod1 allele" can be a mutant rod1 allele or a mutant rod1 gene, which may encode no functional ROD1 protein, or which may encode a mutant ROD1 protein with reduced activity. The gene or allele may also be referred to as an inactivated gene or allele.

A "functional ROD1 gene" or "functional ROD1 allele" as used herein is a ROD1 gene or a ROD1 allele which encodes a functional ROD1 protein.

A "mutant rod1 gene" or "mutant rod1 allele" as used herein refers to any rod1 gene or rod1 allele which is not found in plants in the natural population or breeding population, but which is produced by human intervention such as mutagenesis or gene targeting. A mutant rod1 allele comprises knock-out rod1 alleles, and functional rod1 alleles.

Functional ROD1 protein is a ROD1 protein which has at least 5%, or at least 10%, or at least 15%, or at least 20%, or at least 25%, or at least 30% of the activity of the protein encoded by the *Arabidopsis* ROD1 gene as described in WO2009/111587, as tested, for example, in yeast as described in example 3.

A mutant ROD1 protein with reduced functionality is a ROD1 protein encoded by a mutant rod1 gene which has reduced activity as compared to the corresponding wild-type ROD1 protein encoded by the wild-type ROD1 gene. Said activity may be reduced with at least 10%, or at least 20%, or at least 30%, or at least 40%, or at least 50%, or at least 60%, or at least 70%, or at least 80%, or at least 90%.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an ROD1 gene present within the nuclear genome of a *Brassica juncea* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of an ROD1 protein may thus still be referred to as a "protein". An "isolated protein" is used to refer to a protein that is no longer in its natural environment, for example in vitro or in a recombinant bacterial or plant host cell.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

"Mutagenesis", as used herein, refers to the process in which plant cells (e.g., a plurality of seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet 13:152-156), transposon mutagenesis (McKenzie et al. (2002) Theor Appl Genet 105:23-33), or tissue culture mutagenesis (induction of somaclonal variations), or a combination of two or more of these. Thus, the desired mutagenesis of one or more ROD1 alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, plants are regenerated from the treated cells using known techniques. For instance, the resulting seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant rod1 alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc.

Additional techniques to screen for the presence of specific mutant rod1 alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150. Gene targeting can be used to create mutant rod1 alleles, such as knock-out rod1 alleles.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/ 10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

The current invention is based on the identification of seven ROD1 genes in *Brassica juncea*.

It is a first embodiment of the invention to provide a *Brassica juncea* plant or plant cell, part, seed or progeny thereof, comprising at least one ROD1 gene, characterized in that at least one ROD1 gene is an inactivated or a knock-out rod1 gene. Said at least one ROD1 gene can be, for example, two ROD1 genes, or four ROD1 genes, or seven ROD1 genes, or eight ROD1 genes. In a further embodiment, said plant comprises two knock-out rod1 genes. In yet a further embodiment, said knock-out gene is a knock-out allele of the ROD1 gene encoding a protein having at least 90% sequence identity to SEQ ID No. 2 or SEQ ID No. 4. In a further embodiment, said *Brassica juncea* plant is homozygous for said knock-out rod1 gene.

Said at least one, or two, or four, or seven ROD1 genes can be selected from the group consisting of BjROD1-A1, BjROD1-B1, BjROD1-A2, BjROD1-B2, BjROD1-A3, BjROD1-B3, and BjROD1-B4 or variants thereof. Said eight ROD1 genes can be selected from the group consisting of BjROD1-A1, BjROD1-B1, BjROD1-A2, BjROD1-B2, BjROD1-A3, BjROD1-B3, and BjROD1-B4 or variants thereof and an eighth ROD1 gene which can be a BjROD1-A4 gene.

At least 90% sequence identity as used herein can be at least 90% sequence identity, or at least 95% sequence identity, or at least 98% sequence identity, or can be 100% sequence identity.

A knock-out allele of the ROD1 gene encoding a protein having at least 90% sequence identity to SEQ ID No. 2 or to SEQ ID No. 4 can be a knock-out allele of the ROD1 gene having at least 90% sequence identity, or at least 95% sequence identity, or at least 98% sequence identity, or having 100% sequence identity to SEQ ID No. 1, SEQ ID No. 3, respectively.

Said knock-out allele of said ROD1 gene can be a mutant ROD1 gene comprising one or more nucleotide deletions, insertions or substitutions relative to the wild type nucleic acid sequences. The mutation(s) can result in one or more changes (deletions, insertions and/or substitutions) in the amino acid sequence of the encoded protein is not a functional ROD1 protein.

Nucleic Acid Sequences According to the Invention

Provided are both wild type ROD1 nucleic acid sequences encoding functional ROD1 proteins and mutant rod1 nucleic acid sequences (comprising one or more mutations, preferably mutations which result in no or a significantly reduced biological activity of the encoded ROD1 protein or in no ROD1 protein being produced) of ROD1 genes from *Brassica juncea*.

However, isolated ROD1 and rod1 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of ROD1-A1, ROD1-B1, ROD1-A2, ROD1-B2, ROD1-A3, ROD1-B3, and ROD1-B4 have been isolated from *Brassica juncea*, as depicted in the sequence listing. The wild type ROD1 cDNA sequences are depicted, while the mutant rod1 sequences of these sequences, and of sequences essentially similar to these, are described herein below and in the Examples, with reference to the wild type ROD1 sequences.

A "*Brassica juncea* ROD1-A1 gene", "BjROD1-A1 gene", "*Brassica juncea* ROD1-A1 allele", "BjROD1-A1 allele" or "ROD1-A1 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No. 1.

A "*Brassica juncea* ROD1-B1 gene", "BjROD1-B1 gene", "*Brassica juncea* ROD1-B1 allele", "BjROD1-B1 allele" or "ROD1-B1 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 3.

A "*Brassica juncea* ROD1-A2 gene", "BjROD1-A2 gene", "*Brassica juncea* ROD1-A2 allele", "BjROD1-A2 allele" or "ROD1-A2 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 5.

A "*Brassica juncea* ROD1-B2 gene", "BjROD1-B2 gene", "*Brassica juncea* ROD1-B2 allele", "BjROD1-B2 allele" or "ROD1-B2 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 7.

A "*Brassica juncea* ROD1-A3 gene", "BjROD1-A3 gene", "*Brassica juncea* ROD1-A3 allele", "BjROD1-A3 allele" or "ROD1-A3 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 9.

A "*Brassica juncea* ROD1-B3 gene", "BjROD1-B3 gene", "*Brassica juncea* ROD1-B3 allele", "BjROD1-B3 allele" or "ROD1-B3 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 11.

A "*Brassica juncea* ROD1-B4 gene", "BjROD1-B4 gene", "*Brassica juncea* ROD1-B4 allele", "BjROD1-B4 allele" or "ROD1-B4 from *Brassica juncea*", or variant nucleic acid sequences thereof as used herein refers to a gene, allele or a sequence of which the cDNA sequence has at least 90%, or at least 95%, or at least 98%, or at least 99%, or 100% sequence identity SEQ ID No 13.

A BjROD1-A4 gene is a ROD1 gene which is annotated on the A genome of *Brassica juncea* and homeologous to the BjROD1-B4 gene.

Thus the invention provides both nucleic acid sequences encoding wild type, functional ROD1 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type ROD1 protein. Preferably the mutation(s) in the nucleic acid sequence result in one or more amino acid changes (i.e. in relation to the wild type amino acid sequence one or more amino acids are inserted, deleted and/or substituted) whereby the biological activity of the ROD1 protein is significantly reduced or completely abolished.

Functionality of the ROD1 protein can be tested, for example, in yeast as described in example 3 or as described by Lu et al. (2009) Proc Natl Acad Sci USA 106:18839.

Both endogenous and isolated nucleic acid sequences are provided herein. Also provided are fragments of the ROD1 sequences and ROD1 variant nucleic acid sequences defined above, for use as primers or probes and as components of kits according to another aspect of the invention (see further below). A "fragment" of a ROD1 or rod1 nucleic acid sequence or variant thereof (as defined) may be of various lengths, such as at least 10, 12, 15, 18, 20, 50, 100, 200, 500, 600 contiguous nucleotides of the ROD1 or rod1 sequence (or of the variant sequence).

Wild-type Nucleic Acid Sequences Encoding Wild-type ROD1 Proteins

The nucleic acid sequences depicted in the sequence listing encode wild type ROD1 proteins from *Brassica juncea*. Thus, these sequences are endogenous to the *Brassica juncea* plants from which they were isolated.

Other *Brassica juncea* varieties, breeding lines or wild accessions may be screened for other ROD1 alleles, encoding the same ROD1 proteins or variants thereof. For example, nucleic acid hybridization techniques (e.g. Southern blot analysis, using for example stringent hybridization conditions) or nucleic acid amplification-based techniques such as PCR techniques may be used to identify ROD1 alleles endogenous to other *Brassica juncea* varieties, lines or accessions. To screen such plants, plant organs or tissues for the presence of ROD1 alleles, the ROD1 nucleic acid sequences provided in the sequence listing, or variants or fragments of any of these, may be used. For example whole sequences or fragments may be used as probes or primers. For example specific or degenerate primers may be used to amplify nucleic acid sequences encoding ROD1 proteins from the genomic DNA of the plant, plant organ or tissue. These ROD1 nucleic acid sequences may be isolated and sequenced using standard molecular biology techniques. Bioinformatics analysis may then be used to characterize the allele(s), for example in order to determine which ROD1 allele the sequence corresponds to and which ROD1 protein or protein variant is encoded by the sequence.

In addition, it is understood that ROD1 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below.

Mutant Nucleic Acid Sequences Encoding Mutant ROD1 Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as rod1 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded ROD1 protein (i.e. it is not a "silent mutation"). In another embodiment, the mutation(s) in the nucleic acid sequence result in a significantly reduced or completely abolished biological activity of the encoded ROD1 protein relative to the wild type protein.

The knock-out ROD1 genes may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;

(c) an "insertion mutation" of one or more amino acids, due to one or more codons having been added in the coding sequence of the nucleic acid;
(d) a "deletion mutation" of one or more amino acids, due to one or more codons having been deleted in the coding sequence of the nucleic acid;
(e) a "frameshift mutation", resulting in the nucleic acid sequence being translated in a different frame downstream of the mutation. A frameshift mutation can have various causes, such as the insertion, deletion or duplication of one or more nucleotides;
(f) a splice site mutation, resulting in altered splicing, which results in an altered mRNA processing and, consequently, in an altered encoded protein which contains either deletions, substitutions or insertions of various lengths, possibly combined with premature translation termination.

Thus in one embodiment, nucleic acid sequences comprising one or more of any of the types of mutations described above are provided. In another embodiment, rod1 sequences comprising one or more stop codon (nonsense) mutations, one or more missense mutations, one or more frameshift mutations, and/or one or more splice site mutations are provided. Any of the above mutant nucleic acid sequences are provided per se (in isolated form), as are plants and plant parts comprising such sequences endogenously. In the tables herein below the most preferred rod1 alleles are described.

A range of possible EMS stop codon mutations in the BjROD1-A1, BjROD1-B1, BjROD1-A2, BjROD1-B2, BjROD1-A3, BjROD1-B3 and BjROD1-B4 genes are shown in Tables 1a-g, respectively.

TABLE 1a possible stop codon mutations in BjROD1-A1

| position relative to the genomic sequence (SEQ ID No. 1) | WT codon | AA | position relative to the protein | stop codon | AA |
|---|---|---|---|---|---|
| 397-399 | TGG | TRP | 54 | TAG | STOP |
|  |  |  |  | TAA | STOP |
|  |  |  |  | TGA | STOP |
| 436-438 | TGG | TRP | 67 | TAA | STOP |
|  |  |  |  | TGA | STOP |
|  |  |  |  | TAG | STOP |
| 496-498 | CAG | GLN | 87 | TAG | STOP |
|  |  |  |  | TAA | STOP |
| 628-630 | CAA | GLN | 131 | TAA | STOP |
| 646-648 | TGG | TRP | 137 | TAG | STOP |
|  |  |  |  | TGA | STOP |
|  |  |  |  | TAA | STOP |
| 652-654 | TGG | TRP | 139 | TGA | STOP |
|  |  |  |  | TAA | STOP |
|  |  |  |  | TAG | STOP |
| 673-675 | CGA | ARG | 146 | TGA | STOP |
|  |  |  |  | TAA | STOP |
| 733-735 | CAG | GLN | 166 | TAA | STOP |
|  |  |  |  | TAG | STOP |
| 748-750 | CAG | GLN | 171 | TAA | STOP |
|  |  |  |  | TAG | STOP |
| 862-864 | CAG | GLN | 209 | TAG | STOP |
|  |  |  |  | TAA | STOP |
| 907-909 | CAA | GLN | 224 | TAA | STOP |

TABLE 1b possible stop codon mutations in BjROD1-B1

| position relative to the genomic sequence (SEQ ID No. 3) | WT codon | AA | position relative to the protein | stop codon | AA |
|---|---|---|---|---|---|
| 224-226 | TGG | TRP | 54 | TAG | STOP |
|  |  |  |  | TAA | STOP |
|  |  |  |  | TGA | STOP |
| 263-265 | TGG | TRP | 67 | TAA | STOP |
|  |  |  |  | TGA | STOP |
|  |  |  |  | TAG | STOP |
| 323-325 | CAG | GLN | 87 | TAG | STOP |
|  |  |  |  | TAA | STOP |
| 689-691 | CGG | ARG | 163 | TAA | STOP |
|  |  |  |  | TAG | STOP |
|  |  |  |  | TGA | STOP |
| 734-736 | CAA | GLN | 178 | TAA | STOP |

TABLE 1c possible stop codon mutations in BjROD1-A2

| position relative to the genomic sequence (SEQ ID No. 5) | WT codon | AA | position relative to the protein | stop codon | AA |
|---|---|---|---|---|---|
| 412-414 | TGG | TRP | 57 | TAA | STOP |
|  |  |  |  | TAG | STOP |
|  |  |  |  | TGA | STOP |
| 451-453 | TGG | TRP | 70 | TAA | STOP |
|  |  |  |  | TAG | STOP |
|  |  |  |  | TGA | STOP |
| 511-513 | CAA | GLN | 90 | TAA | STOP |
| 643-645 | CAA | GLN | 134 | TAA | STOP |
| 661-663 | TGG | TRP | 140 | TAG | STOP |
|  |  |  |  | TAA | STOP |
|  |  |  |  | TGA | STOP |
| 667-669 | TGG | TRP | 142 | TAA | STOP |
|  |  |  |  | TGA | STOP |
|  |  |  |  | TAG | STOP |
| 688-690 | CGG | ARG | 149 | TGA | STOP |
|  |  |  |  | TAG | STOP |
|  |  |  |  | TAA | STOP |
| 736-738 | CAG | GLN | 165 | TAA | STOP |
|  |  |  |  | TAG | STOP |
| 751-753 | CAG | GLN | 170 | TAG | STOP |
|  |  |  |  | TAA | STOP |
| 865-867 | CAG | GLN | 208 | TAG | STOP |
|  |  |  |  | TAA | STOP |
| 910-912 | CAA | GLN | 223 | TAA | STOP |

TABLE 1d possible stop codon mutations in BjROD1-B2

| position relative to the genomic sequence (SEQ ID No. 7) | WT codon | AA | position relative to the protein | stop codon | AA |
|---|---|---|---|---|---|
| 298-300 | TGG | TRP | 42 | TAG | STOP |
|  |  |  |  | TAA | STOP |
|  |  |  |  | TGA | STOP |
| 337-339 | TGG | TRP | 55 | TAA | STOP |
|  |  |  |  | TAG | STOP |
|  |  |  |  | TGA | STOP |
| 397-399 | CAG | GLN | 75 | TAA | STOP |
|  |  |  |  | TAG | STOP |

TABLE 1d-continued possible stop codon mutations in BjROD1-B2

| position relative to the genomic sequence (SEQ ID No. 7) | WT codon | WT AA | position relative to the protein | stop codon codon | stop codon AA |
|---|---|---|---|---|---|
| 529-531 | CAA | GLN | 119 | TAA | STOP |
| 547-549 | TGG | TRP | 125 | TAG | STOP |
|  |  |  |  | TGA | STOP |
|  |  |  |  | TAA | STOP |
| 553-555 | TGG | TRP | 127 | TAG | STOP |
|  |  |  |  | TGA | STOP |
|  |  |  |  | TAA | STOP |
| 574-576 | CGG | ARG | 134 | TGA | STOP |
|  |  |  |  | TAG | STOP |
|  |  |  |  | TAA | STOP |
| 634-636 | CAG | GLN | 154 | TAG | STOP |
|  |  |  |  | TAA | STOP |
| 649-651 | CAG | GLN | 159 | TAA | STOP |
|  |  |  |  | TAG | STOP |
| 763-765 | CAG | GLN | 197 | TAG | STOP |
|  |  |  |  | TAA | STOP |
| 808-810 | CAA | GLN | 212 | TAA | STOP |

TABLE 1e possible stop codon mutations in BjROD1-A3

| position relative to the genomic sequence (SEQ ID No. 9) | WT codon | WT AA | position relative to the protein | stop codon codon | stop codon AA |
|---|---|---|---|---|---|
| 161-163 | CAA | GLN | 37 | TAA | STOP |
| 182-184 | CAA | GLN | 44 | TAA | STOP |
| 248-250 | TGG | TRP | 66 | TAA | STOP |
|  |  |  |  | TGA | STOP |
|  |  |  |  | TAG | STOP |
| 287-289 | TGG | TRP | 79 | TGA | STOP |
|  |  |  |  | TAA | STOP |
|  |  |  |  | TAG | STOP |
| 350-352 | CAG | GLN | 100 | TAA | STOP |
|  |  |  |  | TAG | STOP |
| 482-484 | CAA | GLN | 144 | TAA | STOP |
| 500-502 | TGG | TRP | 150 | TAA | STOP |
|  |  |  |  | TAG | STOP |
|  |  |  |  | TGA | STOP |
| 506-508 | TGG | TRP | 152 | TAG | STOP |
|  |  |  |  | TAA | STOP |
|  |  |  |  | TGA | STOP |
| 521-523 | CGA | ARG | 157 | TGA | STOP |
|  |  |  |  | TAA | STOP |
| 527-529 | CGA | ARG | 159 | TAA | STOP |
|  |  |  |  | TGA | STOP |
| 587-589 | CAG | GLN | 179 | TAG | STOP |
|  |  |  |  | TAA | STOP |
| 602-604 | CAG | GLN | 184 | TAG | STOP |
|  |  |  |  | TAA | STOP |
| 761-763 | CAA | GLN | 237 | TAA | STOP |
| 791-793 | CAA | GLN | 247 | TAA | STOP |

TABLE 1f possible stop codon mutations in BjROD1-B3

| position relative to the genomic sequence (SEQ ID No. 11) | WT codon | WT AA | position relative to the protein | stop codon codon | stop codon AA |
|---|---|---|---|---|---|
| 100-102 | CGG | ARG | 11 | TAA | STOP |
|  |  |  |  | TAG | STOP |
|  |  |  |  | TGA | STOP |
| 178-180 | CAA | GLN | 37 | TAA | STOP |
| 199-201 | CAA | GLN | 44 | TAA | STOP |
| 265-267 | TGG | TRP | 66 | TAG | STOP |
|  |  |  |  | TGA | STOP |
|  |  |  |  | TAA | STOP |
| 304-306 | TGG | TRP | 79 | TAA | STOP |
|  |  |  |  | TAG | STOP |
|  |  |  |  | TGA | STOP |
| 367-369 | CAG | GLN | 100 | TAG | STOP |
|  |  |  |  | TAA | STOP |
| 499-501 | CAA | GLN | 144 | TAA | STOP |
| 517-519 | TGG | TRP | 150 | TAA | STOP |
|  |  |  |  | TAG | STOP |
|  |  |  |  | TGA | STOP |
| 523-525 | TGG | TRP | 152 | TAA | STOP |
|  |  |  |  | TGA | STOP |
|  |  |  |  | TAG | STOP |
| 538-540 | CGA | ARG | 157 | TGA | STOP |
|  |  |  |  | TAA | STOP |
| 544-546 | CGA | ARG | 159 | TAA | STOP |
|  |  |  |  | TGA | STOP |
| 604-606 | CAG | GLN | 179 | TAA | STOP |
|  |  |  |  | TAG | STOP |
| 619-621 | CAG | GLN | 184 | TAG | STOP |
|  |  |  |  | TAA | STOP |
| 778-780 | CAA | GLN | 237 | TAA | STOP |
| 808-810 | CAA | GLN | 247 | TAA | STOP |

TABLE 1g possible stop codon mutations in BjROD1-B4

| position relative to the genomic sequence (SEQ ID No. 13) | WT codon | WT AA | position relative to the protein | stop codon codon | stop codon AA |
|---|---|---|---|---|---|
| 29-31 | CAA | GLN | 3 | TAA | STOP |
| 65-67 | TGG | TRP | 15 | TAG | STOP |
|  |  |  |  | TAA | STOP |
|  |  |  |  | TGA | STOP |
| 92-94 | TGG | TRP | 24 | TAA | STOP |
|  |  |  |  | TGA | STOP |
|  |  |  |  | TAG | STOP |
| 131-133 | TGG | TRP | 37 | TGA | STOP |
|  |  |  |  | TAA | STOP |
|  |  |  |  | TAG | STOP |
| 323-325 | CAA | GLN | 101 | TAA | STOP |
| 341-343 | TGG | TRP | 107 | TAG | STOP |
|  |  |  |  | TGA | STOP |
|  |  |  |  | TAA | STOP |
| 347-349 | TGG | TRP | 109 | TAG | STOP |
|  |  |  |  | TGA | STOP |
|  |  |  |  | TAA | STOP |
| 362-364 | CGG | ARG | 114 | TAG | STOP |
|  |  |  |  | TAA | STOP |
|  |  |  |  | TGA | STOP |
| 368-370 | CGA | ARG | 116 | TAA | STOP |
|  |  |  |  | TGA | STOP |
| 428-430 | CAG | GLN | 136 | TAG | STOP |
|  |  |  |  | TAA | STOP |

TABLE 1g-continued possible stop codon mutations in BjROD1-B4

| position relative to the genomic sequence (SEQ ID No. 13 | WT codon | AA | position relative to the protein | stop codon | AA |
|---|---|---|---|---|---|
| 557-559 | CAG | GLN | 179 | TAA | STOP |
|  |  |  |  | TAG | STOP |
| 602-604 | CAG | GLN | 194 | TAA | STOP |
|  |  |  |  | TAG | STOP |
| 722-724 | CAA | GLN | 234 | TAA | STOP |

Obviously, mutations are not limited to the ones shown in the above tables and it is understood that analogous STOP mutations may be present in rod1 alleles other than those depicted in the sequence listing and referred to in the tables above. Not only stopcodon mutations, but also mutations resulting in an amino acid substitution may lead to proteins with reduced functionality or with no detectable activity. Amino acids that, when substituted, may lead to proteins with reduced activity are Glu at position 144, Thr at position 150, Arg at position 160, Gly at position 161, and Pro at position 172 of the BjROD1-A1 protein, or Glu at position 142, Thr at position 148, Arg at position 158, and Pro at position 169 of the BjROD1-B1 protein.

Wild-type and mutant ROD1 nucleic acid sequences from the A-genome as described herein, such as BjROD1-A1, BjROD1-A2, and BjROD1-A3 are also suitable to use in other *Brassica* species comprising an A genome, such as *Brassica napus* and *Brassica rapa*.

Wild-type and mutant ROD1 nucleic acid sequences from the B-genome as described herein, such as BnROD1-131, BnROD1-B2, BnROD1-B3, and BnROD1-B4 are also suitable to use in other *Brassica* species comprising an B genome, such as *Brassica carinata* and *Brassica nigra*.

Amino Acid Sequences According to the Invention

Provided are both wild type ROD1 amino acid sequences and mutant ROD1 amino acid sequences (comprising one or more mutations, preferably mutations which result in a significantly reduced or no biological activity of the ROD1 protein) from *Brassica juncea*. In addition, mutagenesis methods can be used to generate mutations in wild type ROD1 alleles, thereby generating mutant alleles which can encode further mutant ROD1 proteins. In one embodiment the wild type and/or mutant ROD1 amino acid sequences are provided within a *Brassica juncea* plant (i.e. endogenously). However, isolated ROD1 amino acid sequences (e.g. isolated from the plant or made synthetically), as well as variants thereof and fragments of any of these are also provided herein.

Amino acid sequences of *Brassica juncea* ROD1-1 and ROD1-2 proteins have been isolated as depicted in the sequence listing. The wild type ROD1 sequences are depicted, while the mutant ROD1 sequences of these sequences, and of sequences essentially similar to these, are described herein below, with reference to the wild type ROD1 sequences.

"*Brassica juncea* ROD1-A1 amino acid sequences" or "BjROD1-A1 amino acid sequences" or variant amino acid sequences thereof according to the invention are amino acid sequences having at least 95%, 98%, 99% or 100% sequence identity with SEQ ID NO: 2. These amino acid sequences may also be referred to as being "essentially similar" or "essentially identical" to the ROD1 sequences provided in the sequence listing.

"*Brassica juncea* ROD1-B1 amino acid sequences" or "BjROD1-B1 amino acid sequences" or variant amino acid sequences thereof according to the invention are amino acid sequences having at least 95%, 98%, 99% or 100% sequence identity with SEQ ID NO: 4. These amino acid sequences may also be referred to as being "essentially similar" or "essentially identical" to the ROD1 sequences provided in the sequence listing.

"*Brassica juncea* ROD1-A2 amino acid sequences" or "BjROD1-A2 amino acid sequences" or variant amino acid sequences thereof according to the invention are amino acid sequences having at least 95%, 98%, 99% or 100% sequence identity with SEQ ID NO: 6. These amino acid sequences may also be referred to as being "essentially similar" or "essentially identical" to the ROD1 sequences provided in the sequence listing.

"*Brassica juncea* ROD1-B2 amino acid sequences" or "BjROD1-B2 amino acid sequences" or variant amino acid sequences thereof according to the invention are amino acid sequences having at least 95%, 98%, 99% or 100% sequence identity with SEQ ID NO: 8. These amino acid sequences may also be referred to as being "essentially similar" or "essentially identical" to the ROD1 sequences provided in the sequence listing.

"*Brassica juncea* ROD1-A3 amino acid sequences" or "BjROD1-A3 amino acid sequences" or variant amino acid sequences thereof according to the invention are amino acid sequences having at least 95%, 98%, 99% or 100% sequence identity with SEQ ID NO: 10. These amino acid sequences may also be referred to as being "essentially similar" or "essentially identical" to the ROD1 sequences provided in the sequence listing.

"*Brassica juncea* ROD1-B3 amino acid sequences" or "BjROD1-B3 amino acid sequences" or variant amino acid sequences thereof according to the invention are amino acid sequences having at least 95%, 98%, 99% or 100% sequence identity with SEQ ID NO: 12. These amino acid sequences may also be referred to as being "essentially similar" or "essentially identical" to the ROD1 sequences provided in the sequence listing.

"*Brassica juncea* ROD1-B4 amino acid sequences" or "BjROD1-B4 amino acid sequences" or variant amino acid sequences thereof according to the invention are amino acid sequences having at least 95%, 98%, 99% or 100% sequence identity with SEQ ID NO: 14. These amino acid sequences may also be referred to as being "essentially similar" or "essentially identical" to the ROD1 sequences provided in the sequence listing.

"*Brassica juncea* ROD1-A4 amino acid sequences" or "BjROD1-A4 amino acid sequences" or variant amino acid sequences thereof according to the invention are amino acid sequences encoded by the BjROD1-A4 gene. These amino acid sequences may also be referred to as being "essentially similar" or "essentially identical" to ROD1-A4.

Thus, the invention provides both amino acid sequences of wild type proteins, including variants and fragments thereof (as defined further below), as well as mutant amino acid sequences of any of these, whereby the mutation in the amino acid sequence preferably results in a significant reduction in or a complete abolishment of the biological activity of the ROD1 protein as compared to the biological activity of the corresponding wild type ROD1 protein.

Both endogenous and isolated amino acid sequences are provided herein. Also provided are fragments of the ROD1 amino acid sequences and ROD1 variant amino acid sequences defined above. A "fragment" of a ROD1 amino acid sequence or variant thereof (as defined) may be of various lengths, such as at least 10, 12, 15, 18, 20, 50, 100, 150, 175, 180 contiguous amino acids of the ROD1 sequence (or of the variant sequence).

Amino Acid Sequences of Wild-type ROD1 Proteins

The amino acid sequences depicted in the sequence listing are wild type ROD1 proteins from *Brassica juncea*. Thus, these sequences are endogenous to the *Brassica juncea* plants from which they were isolated. Other *Brassica juncea* varieties, breeding lines or wild accessions may be screened for other functional ROD1 proteins with the same amino acid sequences or variants thereof, as described above.

In addition, it is understood that ROD1 amino acid sequences and variants thereof (or fragments of any of these) may be identified in silico, by screening amino acid databases for essentially similar sequences. Fragments of amino acid molecules according to the invention are also provided.

Amino Acid Sequences of Mutant ROD1 Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the ROD1 protein relative to the wild type protein. As described above, basically, any mutation which results in a protein comprising at least one amino acid insertion, deletion and/or substitution relative to the wild type protein can lead to significantly reduced or no biological activity.

Thus in one embodiment, mutant ROD1 proteins are provided comprising one or more deletion or insertion mutations, whereby the deletion(s) or insertion(s) result(s) in a mutant protein which has significantly reduced or no activity. Such mutant ROD1 proteins are ROD1 proteins wherein at least 1, at least 2, 3, 4, 5, 10, 20, 30, 50, 100, 150, 200 or more amino acids are deleted, inserted or substituted as compared to the wild type ROD1 protein, whereby the deletion(s) or insertion(s) result(s) in a mutant protein which has significantly reduced or no activity.

In another embodiment, mutant ROD1 proteins are provided which are truncated whereby the truncation results in a mutant protein that has significantly reduced or no activity.

In yet another embodiment, mutant ROD1 proteins are provided comprising one or more substitution mutations, whereby the substitution(s) result(s) in a mutant protein that has significantly reduced or no activity.

In a further embodiment, a transgenic *Brassica juncea* plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells.

Said at least one ROD1 gene can be, for example, two ROD1 genes, or four ROD1 genes, or seven ROD1 genes, or eight ROD1 genes.

Said at least one, or two, or four, or seven ROD1 genes can be selected from the group consisting of BjROD1-A1, BjROD1-B1, BjROD1-A2, BjROD1-B2, BjROD1-A3, BjROD1-B3, and BjROD1-B4 or variants thereof. Said eight ROD1 genes can be selected from the group consisting of B/ROD1-A1, BjROD1-B1, BjROD1-A2, BjROD1-B2, BjROD1-A3, BjROD1-B3, and BjROD1-B4 or variants thereof and an eighth ROD1 gene which can be a BjROD1-A4 gene.

In another embodiment, said RNA molecule is inhibitory to a ROD1 gene encoding a protein having at least 90% sequence identity to SEQ ID No. 2, or is inhibitory to a ROD1 gene encoding a protein having at least 90% sequence identity to SEQ ID No. 4, is inhibitory to both a ROD1 gene encoding a protein having at least 90% sequence identity to SEQ ID No. 2 and to a ROD1 gene encoding a protein having at least 90% sequence identity to SEQ ID No. 4.

An RNA molecule inhibitory to at least one ROD1 gene can be an RNA that downregulates ROD1 gene expression by decreasing the levels of ROD1 mRNAs available for translation. Said RNA can downregulate ROD1 gene expression through, for example, co-suppression (sense RNA suppression), antisense RNA, double-stranded RNA (dsRNA) or microRNA (miRNA), or ta-siRNA.

Said RNA molecule inhibitory to at least one ROD1 gene is characterized tin that said RNA molecule comprises a region with sufficient homology to said ROD1 genes to be downregulated.

Sufficient homology to the ROD1 genes to be downregulated as used herein means that the transcribed DNA region (and resulting RNA molecule) comprises at least 20 consecutive nucleotides having at least 95% sequence identity to the nucleotide sequence or the complement of the nucleotide of the ROD1 gene to be downregulated.

Said RNA molecule inhibitory to at least one ROD1 gene may be a sense RNA molecule capable of down-regulating expression of one or more functional ROD1 genes by co-suppression. Said RNA molecule comprises at least 20 consecutive nucleotides having at least 95% sequence identity to the nucleotide sequence of one or more ROD1 genes present in the plant cell or plant.

Said RNA molecule inhibitory to at least one ROD1 gene may further be an antisense RNA molecule capable of down-regulating expression of one or more functional ROD1 genes. Said RNA molecule comprises at least 20 consecutive nucleotides having at least 95% sequence identity to the complement of the nucleotide sequence of one or more functional ROD1 genes present in the plant cell or plant.

The minimum nucleotide sequence of the antisense or sense RNA region of about 20 nt of the ROD1 gene may be comprised within a larger RNA molecule, varying in size from 20 nt to a length equal to the size of the target gene. The mentioned antisense or sense nucleotide regions may thus be about from about 21 nt to about 1300 nt long, such as 21 nt, 40 nt, 50 nt, 100 nt, 200 nt, 300 nt, 500 nt, 1000 nt, or even about 1300 nt or larger in length. Moreover, it is not required for the purpose of the invention that the nucleotide sequence of the used inhibitory ROD1 RNA molecule or the encoding region of the transgene, is completely identical or complementary to the endogenous ROD1 gene the expression of which is targeted to be reduced in the plant cell. The longer the sequence, the less stringent the requirement for the overall sequence identity is. Thus, the sense or antisense regions may have an overall sequence identity of about 40% or 50 or 60% or 70% or 80% or 90% or 100% to the nucleotide sequence of the endogenous ROD1 gene or the complement thereof. However, as mentioned, antisense or sense regions should comprise a nucleotide sequence of 20 consecutive nucleotides having about 95 to about 100% sequence identity to the nucleotide sequence of the endogenous ROD1 gene. The stretch of about 95 to about 100% sequence identity may be about 50, 75 or 100 nt. It will be clear that all combinations between mentioned length and sequence identity can be made, both in sense and/or antisense orientation.

The abovementioned chimeric gene may further comprise DNA elements which result in the expression of aberrant, non-polyadenylated ROD1 inhibitory RNA molecules. One such DNA element suitable for that purpose is a DNA region encoding a self-splicing ribozyme, as described in WO 00/01133. The efficiency may also be enhanced by providing the generated RNA molecules with nuclear localization or retention signals as described in WO 03/076619.

Said RNA molecule inhibitory to at least one ROD1 gene may further be a double-stranded RNA molecule capable of down-regulating ROD1 gene expression. Upon transcription of the DNA region the RNA is able to form dsRNA molecule through conventional base paring between a sense and antisense region, whereby the sense and antisense region are nucleotide sequences as hereinbefore described. dsRNA-encoding ROD1 expression-reducing chimeric genes according to the invention may further comprise an intron, such as a heterologous intron, located e.g. in the spacer sequence between the sense and antisense RNA regions in accordance with the disclosure of WO 99/53050. To achieve the construction of such a transgene, use can be made of the vectors described in WO 02/059294 A1.

Said RNA molecule inhibitory to at least one ROD1 gene may further be a pre-miRNA molecule which is processed into a miRNA capable of guiding the cleavage of ROD1 mRNA. miRNAs are small endogenous RNAs that regulate gene expression in plants, but also in other eukaryotes. In plants, these about 21 nucleotide long RNAs are processed from the stem-loop regions of long endogenous pre-miR-NAs by the cleavage activity of DICERLIKE1 (DCL1). Plant miRNAs are highly complementary to conserved target mRNAs, and guide the cleavage of their targets. miRNAs appear to be key components in regulating the gene expression of complex networks of pathways involved inter alia in development.

As used herein, a "miRNA" is an RNA molecule of about 20 to 22 nucleotides in length which can be loaded into a RISC complex and direct the cleavage of a target RNA molecule, wherein the target RNA molecule comprises a nucleotide sequence essentially complementary to the nucleotide sequence of the miRNA molecule whereby one or more of the following mismatches may occur:

A mismatch between the nucleotide at the 5' end of said miRNA and the corresponding nucleotide sequence in the target RNA molecule;

A mismatch between any one of the nucleotides in position 1 to position 9 of said miRNA and the corresponding nucleotide sequence in the target RNA molecule;

Three mismatches between any one of the nucleotides in position 12 to position 21 of said miRNA and the corresponding nucleotide sequence in the target RNA molecule provided that there are no more than two consecutive mismatches.

No mismatch is allowed at positions 10 and 11 of the miRNA (all miRNA positions are indicated starting from the 5' end of the miRNA molecule).

As used herein, a "pre-miRNA" molecule is an RNA molecule of about 100 to about 200 nucleotides, preferably about 100 to about 130 nucleotides which can adopt a secondary structure comprising a dsRNA stem and a single stranded RNA loop and further comprising the nucleotide sequence of the miRNA and its complement sequence of the miRNA* in the double-stranded RNA stem. Preferably, the miRNA and its complement are located about 10 to about 20 nucleotides from the free ends of the miRNA dsRNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* do not need to be perfect and about 1 to 3 bulges of unpaired nucleotides can be tolerated. The secondary structure adopted by an RNA molecule can be predicted by computer algorithms conventional in the art such as mFold, UNAFold and RNAFold. The particular strand of the dsRNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

Said RNA molecule inhibitory to at least one ROD1 gene may further be a ta-siRNAs as described in WO2006/074400.

Said RNA molecule may be inhibitory to all ROD1 genes present in said *Brassica juncea* plant. For example, said RNA molecule is inhibitory to a ROD1 gene encoding a protein having at least 90% sequence identity to SEQ ID No. 2 and SEQ ID No. 4, such as a ROD1 gene having at least 90% sequence identity, or at least 95% sequence identity, or at least 98% sequence identity or having 100% sequence identity to SEQ ID No. 1 or SEQ ID No. 3, respectively.

Said RNA molecule may further be inhibitory to only one ROD1 gene, such as the ROD1 genes encoding a protein having at least 90% sequence identity to SEQ ID No. 2 only, such as a ROD1 gene having at least 90% sequence identity, or at least 95% sequence identity, or at least 98% sequence identity or having 100% sequence identity to SEQ ID No. 1, or to the ROD1 gene encoding a protein having at least 90% sequence identity to SEQ ID No. 4 only, such as a ROD1 gene having at least 90% sequence identity, or at least 95% sequence identity, or at least 98% sequence identity or having 100% sequence identity to SEQ ID No. 3.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

A "heterologous promoter" as used herein refers to a promoter which is not normally associated in its natural context with the coding DNA region operably linked to it in the DNA molecules according to the invention.

Said plant-expressible promoter can, for example, be a constitutive promoter, such as the CaMV35S promoter (Harpster et al. (1988) *Mol Gen Genet.* 212(1):182-90), or a seed-specific promoter, such as the *Arabidopsis* oleosin promoter (WO1998/045461).

Constitutive promoters are well known in the art, and include the CaMV35S promoter (Harpster et al. (1988) *Mol Gen Genet.* 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the *Agrobacterium tumefaciens* Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant Mol. Biol. 18:675).

Seed specific promoters are well known in the art, including the *Arabidopsis* oleosin promoter (WO1998/045461), the USP promoter from *Vicia faba* described in DE10211617; the promoter sequences described in WO2009/073738; promoters from *Brassica napus* for seed specific gene expression as described in WO2009/077478; the plant seed specific promoters described in US2007/0022502; the plant seed specific promoters described in WO03/014347; the seed specific promoter described in WO2009/125826; the promoters of the omega_3 fatty acid desaturase family described in WO2006/005807 and the like.

A "transcription termination and polyadenylation region" as used herein is a sequence that drives the cleavage of the nascent RNA, whereafter a poly(A) tail is added at the resulting RNA 3' end, functional in plants. Transcription termination and polyadenylation signals functional in plants include, but are not limited to, 3'nos, 3'35S, 3'his and 3'g7.

In a further embodiment, the seeds of the plants according to the invention have increased levels of C18:1, or increased levels of C18:1 and decreased levels of C18:2, or increased levels of C18:1 and decreased levels of SATS.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in *Brassica juncea* seed oil, comprising modulating the expression of a ROD1 gene. In yet another embodiment, a method is provided for increasing the C18:1 levels in *Brassica juncea* seed oil, comprising the steps of introducing or providing an chimeric gene to a *Brassica juncea* plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

"C18:1", also referred to as "oleic acid", "cis-9-octadecenoic", "18:1", "18:1 (n-9)", "9c-18:1" or "18:1cis $\Delta^9$" as used herein, refers to a monounsaturated omega-9 fatty acid, with the IUPAC name (9Z)-Octadec-9-enoic acid.

"C18:2", also referred to as "linoleic acid", "cis-9,12-octadecadienoic acid", "18:2", "18:2 (n-6)", "9c12c-18:1 or "18:2cis $\Delta^{9,12}$", as used herein, refers to a carboxylic acid with an 18-carbon chain and two double bonds with the IUPAC name cis, cis-9,12-Octadecadienoic acid.

SATS, as used herein, refers to saturated fatty acids, which refers to the sum of the levels of C12:0, C14:0, C16:0, C18:0, C20:0, C22:0 and C24:0.

Increasing the C18:1 levels or increased C18:1 levels in seed oil can be an increase of C18:1 levels with at least 2%, or at least 5%, or at least 8%, or at least 10%, or at least 12%. Said increase is an increase with respect to C18:1 levels as obtained in control plants.

Decreased levels of C18:2 can be a decrease of C18:2 levels in seed oil with at least 2%, or at least 5%, or at least 8%, or at least 10%, or at least 20%, or at least 30%.

Decreased levels of SATS can be a decrease in the levels of SATS in seed oil with at least 2%, or at least 3%, or at least 5%. A decrease in the levels of SATS refers to a decrease in the total levels of the sum of C16:0, C18:0, C20:0, C22:0 and C24:0. As such, a decrease in the levels of SATS can be a decrease in the levels of only one of the saturated fatty acids, or of more than one of the saturated fatty acids.

Optionally, the increase of the C18:1 levels or decrease of the C18:2 or SATS in seeds or in seed oil is higher than an increase in C18:1 levels or decrease of the C18:2 or SATS in membrane lipids. For example, the levels of C18:1 are increased, or the C18:2 levels or SATS are increased in the seeds, but the C18:1, C18:2 and SATS levels are unchanged in membrane lipids.

C18:1, C18:2 and SATS levels can be measured as described herein, such as, for example, using the methods as described in Examples 4 and 5.

The "control plant" as used herein is generally a plant of the same species which has wild-type levels of ROD1. "Wild-type levels of ROD1" as used herein refers to the typical levels of ROD1 protein in a plant as it most commonly occurs in nature. Said control plant does contain an RNA molecule inhibitory to ROD1, and in which the ROD1 genes are wild-type ROD1 genes.

A chimeric gene can be provided to a plant or plant cell using methods well-known in the art. Methods to provide plant cells with a chimeric are not deemed critical for the current invention and any method to provide plant cells with a chimeric gene suitable for a particular plant species can be used. Such methods are well known in the art and include Agrobacterium-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. Said chimeric can be transiently introduced into the plant cell or plant cell nucleus. Said chimeric may be stably integrated into the genome of said plant cell, resulting in a transformed plant cell. The transformed plant cells obtained in this way may then be regenerated into mature fertile transformed plants.

The obtained transformed plant, comprising the RNA molecule inhibitory to at least one ROD1 gene, can be used in a conventional breeding scheme to produce more transformed plants with the same characteristics or to introduce the transgene according to the invention in other varieties of the same or related plant species, or in hybrid plants. Seeds obtained from the transformed plants contain the chimeric genes of the invention as a stable genomic insert and are also encompassed by the invention.

In again another embodiment, a method is provided for increasing the C18:1 levels in seed oil, comprising the steps of treating seeds or plant material with a mutagenic chemical substance or with ionizing radiation; identifying plants with a mutated rod1 gene, wherein the ROD1 gene, prior to being mutated, encodes a polypeptide having at least 90% sequence identity to SEQ ID No. 2 or to SEQ ID No. 4; and selecting a plant with an increased level of C18:1 in the seeds compared to a plant in which the ROD1 gene is not mutated.

Said ROD1 gene, prior to being mutated, can be, for example, a ROD1 gene having at least 90% sequence identity, or at least 95% sequence identity, or at least 98% sequence identity or having 100% sequence identity to SEQ ID No. 1, or SEQ ID No. 3.

In a further embodiment, a method is provided for obtaining a *Brassica juncea* plant with increased levels of C18:1 in the seeds comprising the step of introducing a knock-out allele of a ROD1 gene in said *Brassica juncea* plant, and selecting said *Brassica juncea* plant with increased levels of C18:1 in the seeds for the presence of said knock-out allele of a ROD1 gene by analyzing genomic DNA from said plant for the presence of at least one molecular marker, wherein said at least one molecular marker is linked to said knock-out allele of a ROD1 gene.

Introducing said knock-out allele of ROD1 can occur through mutagenesis or gene targeting as described above. Introducing said knock-out allele can also occur through introduction of a knock-out ROD1 allele from one plant into another.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Said genomic DNA can be provided by isolating genomic DNA from said biological sample. Isolating genomic DNA refers to isolating a biological sample comprising genomic DNA from, such as isolating part of a tissue, such as, for example part of a leaf. Isolating genomic DNA from said biological sample can, but does not need to comprise, purification of genomic DNA from said sample.

Yet another embodiment provides a kit for the detection of a knock-out allele of a ROD1 gene in *Brassica juncea* DNA samples, wherein said kit comprises one or more PCR primer pairs, which are able to amplify a DNA marker linked to said knock-out allele of a ROD1 gene. In yet another embodiment, said kit further comprises one or more probes.

In a specific embodiment, said knock-out allele of a ROD1 gene is a mutant ROD1 allele.

In a further embodiment, a method is provided for determining the zygosity status of a mutant ROD1 allele in a *Brassica juncea* plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides method for transferring at least one knock-out ROD1 allele from one *Brassica juncea* plant to another *Brassica juncea* plant comprising the steps of identifying a first *Brassica juncea* plant comprising at least one knock-out ROD1 allele; crossing the first *Brassica juncea* plant with a second *Brassica juncea* plant not comprising the at least one knock-out ROD1 allele and collecting F1 hybrid seeds from the cross; optionally, identifying F1 *Brassica juncea* plants comprising the at least one knock-out ROD1 allele; backcrossing F1 *Brassica juncea* plants comprising the at least one knock-out ROD1 allele with the second plant not comprising the at least one knock-out ROD1 allele for at least one generation (x) and collecting BCx seeds from the crosses; identifying in every generation BCx *Brassica juncea* plants comprising the at least one knock-out ROD1 allele by analyzing genomic DNA of said BCx plants for the presence of at least one molecular marker, wherein the at least one molecular marker is linked to said knock-out ROD1 allele.

A molecular marker which is linked to said knock-out allele of a ROD1 gene or said mutant ROD1 allele can comprise on or more primers or probes that specifically detect said knock-out allele of said ROD1 gene as described herein below.

Methods According to the Invention Mutant rod1 alleles may be generated (for example induced by mutagenesis) and/or identified using a range of methods, which are conventional in the art, for example using nucleic acid amplification based methods to amplify part or all of the rod1 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant ROD1 alleles, using techniques which are conventional in the art, for example nucleic acid amplification based techniques, such as polymerase chain reaction (PCR) based techniques (amplification of the rod1 alleles) or hybridization based techniques, e.g. Southern blot analysis, BAC library screening, and the like, and/or direct sequencing of rod1 alleles. To screen for the presence of point mutations (so called Single Nucleotide Polymorphisms or SNPs) in mutant ROD1 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type ROD1 allele results in the presence of one or more deleted, inserted, or substituted nucleotides (hereinafter called "mutation region") in the resulting mutant ROD1 allele. The mutant ROD1 allele can thus be characterized by the location and the configuration of the one or more deleted, inserted, or substituted nucleotides in the wild type ROD1 allele. The site in the wild type ROD1 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) ROD1 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) ROD1 allele which is located either immediately upstream of and contiguous with (5' flanking region or sequence") or immediately downstream of and contiguous with (3' flanking region or sequence") the mutation region in the mutant ROD1 allele (or in the corresponding wild type ROD1 allele). A "joining region" as used herein refers to a DNA region in the mutant (or the corresponding wild type) ROD1 allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant ROD1 allele or the plant or plant material comprising a specific mutant ROD1 allele, or products which comprise plant material comprising a specific mutant ROD1 allele are based on the specific genomic characteristics of the specific mutant ROD1 allele as compared to the genomic characteristics of the corresponding wild type ROD1 allele, such as, a specific restriction map of the genomic region comprising the mutation region, molecular markers comprising primers and/or probes as described below, or the sequence of the flanking and/or mutation regions.

Once a specific mutant ROD1 allele has been sequenced, molecular markers, such as primers and probes can be developed which specifically recognize a sequence within the 5' flanking, 3' flanking and/or mutation regions of the mutant ROD1 allele in the nucleic acid (DNA or RNA) of a sample by way of a molecular biological technique. For instance an amplification method can be developed to identify the mutant ROD1 allele in biological samples (such as samples of plants, plant material or products comprising plant material). Such an amplification is based on at least two specific "primers": one recognizing a sequence within the 5' or 3' flanking region of the mutant ROD1 allele and the other recognizing a sequence within the 3' or 5' flanking region of the mutant ROD1 allele, respectively; or one recognizing a sequence within the 5' or 3' flanking region of the mutant ROD1 allele and the other recognizing a sequence within the mutation region of the mutant ROD1 allele; or one recognizing a sequence within the 5' or 3' flanking region of the mutant ROD1 allele and the other recognizing a sequence spanning the joining region between the 3' or 5' flanking region and the mutation region of the specific mutant ROD1 allele (as described further below), respectively.

The primers preferably have a sequence of between 15 and 35 nucleotides which under optimized amplification conditions "specifically recognize" a sequence within the 5' or 3' flanking region, a sequence within the mutation region, or a sequence spanning the joining region between the 3' or 5' flanking and mutation regions of the specific mutant ROD1 allele, so that a specific fragment ("mutant ROD1 specific fragment" or discriminating amplicon) is amplified from a nucleic acid sample comprising the specific mutant ROD1 allele. This means that only the targeted mutant ROD1 allele, and no other sequence in the plant genome, is amplified under optimized amplification conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the STOP codon mutations indicated in the above Tables or the substitution mutations indicated above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant ROD1 allele or the complement thereof (i.e., for example, the sequence of nucleotides inserted or substituted in the ROD1 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be no longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense, frameshift or splice site mutations in the ROD1 genes of the invention described above and the sequence of the non-sense, mis-sense, frameshift or splice site mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇌T; G⇌C) and reading the sequence in the 5' to 3' direction, i.e. in opposite direction of the represented nucleotide sequence.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant ROD1 allele, provided the mismatches still allow specific identification of the specific mutant ROD1 allele with these primers under optimized amplification conditions. The range of allowable mismatches however, can easily be determined experimentally and are known to a person skilled in the art.

Detection and/or identification of a "mutant ROD1 specific fragment" can occur in various ways, e.g., via size estimation after gel or capillary electrophoresis or via fluorescence-based detection methods. The mutant ROD1 specific fragments may also be directly sequenced. Other sequence specific methods for detection of amplified DNA fragments are also known in the art.

Standard nucleic acid amplification protocols, such as PCR protocols are described in the art, such as in 'PCR Applications Manual" (Roche Molecular Biochemicals, 2nd Edition, 1999) and other references. The optimal conditions for the amplification, including the sequence of the specific primers, is specified in a "PCR identification protocol" for each specific mutant ROD1 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify a mutant ROD1 specific fragment that can be used as a "specific probe" for identifying a specific mutant ROD1 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant ROD1 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant ROD1 allele (hereinafter referred to as "mutant ROD1 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant ROD1 allele.

Specific probes suitable for the invention may be the following:

oligonucleotides ranging in length from 13 nt to about 1000 nt, comprising a nucleotide sequence of at least 13 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or oligonucleotides ranging in length from 13 nt to about 1000 nt, comprising a nucleotide sequence of at least 13 consecutive nucleotides selected from the mutation sequence of a specific mutant ROD1 allele or the complement thereof (i.e., for example, the sequence of nucleotides inserted or substituted in the ROD1 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be no longer than 50, more preferably not longer than 25 or even no longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense, frameshift or splice site mutations in the ROD1 genes of the invention described above and the sequence of the non-sense, missense, frameshift or splice site mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Detection and/or identification of a "mutant ROD1 specific region" hybridizing to a specific probe can occur in various ways, e.g., via size estimation after gel electrophoresis or via fluorescence-based detection methods. Other sequence specific methods for detection of a "mutant ROD1 specific region" hybridizing to a specific probe are also known in the art.

Alternatively, plants or plant parts comprising one or more mutant rod1 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant rod1 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in ROD1 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant rod1 alleles. As for the mutagenesis techniques above, preferably Brassica species are screened which comprise an A and/or a B genome, so that the identified rod1 allele can subsequently be introduced into other Brassica species, such as Brassica juncea, by crossing (inter- or intraspecific crosses) and selection. In ECOTILLING natural polymorphisms in breeding lines or related species are screened for by the TILLING methodology described above, in which individual or pools of plants are used for PCR amplification of the rod1 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant rod1 alleles (and plants comprising one or more of these) can be identified. The desired mutant alleles can then be combined with the desired wild type alleles by crossing and selection methods as described further below. Finally a single plant comprising the desired number of mutant rod1 and the desired number of wild type ROD1 alleles is generated.

Oligonucleotides suitable as PCR primers or specific probes for detection of a specific mutant ROD1 allele can also be used to develop methods to determine the zygosity status of the specific mutant ROD1 allele.

To determine the zygosity status of a specific mutant ROD1 allele, a nucleic acid amplification-based assay can be developed to determine the presence of a mutant and/or corresponding wild type ROD1 specific allele:

To determine the zygosity status of a specific mutant ROD1 allele, two primers specifically recognizing the wild-type ROD1 allele can be designed in such a way that they are directed towards each other and have the mutation region located in between the primers. These primers may be primers specifically recognizing the 5' and 3' flanking sequences, respectively. This set of primers allows simultaneous diagnostic amplification of the mutant, as well as of the corresponding wild type ROD1 allele.

Alternatively, to determine the zygosity status of a specific mutant ROD1 allele, two primers specifically recognizing the wild-type ROD1 allele can be designed in such a way that they are directed towards each other and that one of them specifically recognizes the mutation region. These primers may be primers specifically recognizing the sequence of the 5' or 3' flanking region and the mutation region of the wild type ROD1 allele, respectively. This set of primers, together with a third primer which specifically recognizes the sequence of the mutation region in the mutant ROD1 allele, allow simultaneous diagnostic amplification of the mutant ROD1 gene, as well as of the wild type ROD1 gene.

Alternatively, to determine the zygosity status of a specific mutant ROD1 allele, two primers specifically recognizing the wild-type ROD1 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type ROD1 allele, respectively. This set of primers, together with a third primer which specifically recognizes the joining region between the mutation region and the 3' or 5' flanking region of the mutant ROD1 allele, respectively, allow simultaneous diagnostic amplification of the mutant ROD1 gene, as well as of the wild type ROD1 gene.

Alternatively, the zygosity status of a specific mutant ROD1 allele can be determined by using alternative primer sets that specifically recognize mutant and wild type ROD1 alleles.

If the plant is homozygous for the mutant ROD1 gene or the corresponding wild type ROD1 gene, the diagnostic amplification assays described above will give rise to a single amplification product typical, preferably typical in length, for either the mutant or wild type ROD1 allele. If the plant is heterozygous for the mutant ROD1 allele, two specific amplification products will appear, reflecting both the amplification of the mutant and the wild type ROD1 allele.

Identification of the wild type and mutant ROD1 specific amplification products can occur e.g. by size estimation after gel or capillary electrophoresis (e.g. for mutant ROD1 alleles comprising a number of inserted or deleted nucleotides which results in a size difference between the fragments amplified from the wild type and the mutant ROD1 allele, such that said fragments can be visibly separated on a gel); by evaluating the presence or absence of the two different fragments after gel or capillary electrophoresis, whereby the diagnostic amplification of the mutant ROD1 allele can, optionally, be performed separately from the diagnostic amplification of the wild type ROD1 allele; by direct sequencing of the amplified fragments; or by fluorescence-based detection methods.

Alternatively, to determine the zygosity status of a specific mutant ROD1 allele, a hybridization-based assay can be developed to determine the presence of a mutant and/or corresponding wild type ROD1 specific allele:

To determine the zygosity status of a specific mutant ROD1 allele, two specific probes recognizing the wild-type ROD1 allele can be designed in such a way that each probe specifically recognizes a sequence within the ROD1 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type ROD1 allele.

Alternatively, to determine the zygosity status of a specific mutant ROD1 allele, two specific probes recognizing the wild-type ROD1 allele can be designed in such a way that one of them specifically recognizes a sequence within the ROD1 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type ROD1 allele, respectively. The use of one or, preferably, both of these probes, optionally, together with a third probe which specifically recognizes the sequence of the mutation region in the mutant ROD1 allele, allow diagnostic hybridization of the mutant and of the wild type ROD1 gene.

Alternatively, to determine the zygosity status of a specific mutant ROD1 allele, a specific probe recognizing the wild-type ROD1 allele can be designed in such a way that the probe specifically recognizes the joining region between the 5' or 3' flanking region, preferably the 5' flanking region, and the mutation region of the wild type ROD1 allele.

This probe, optionally, together with a second probe that specifically recognizes the joining region between the 5' or 3' flanking region, preferably the 5' flanking region, and the mutation region of the mutant ROD1 allele, allows diagnostic hybridization of the mutant and of the wild type ROD1 gene.

Alternatively, the zygosity status of a specific mutant ROD1 allele can be determined by using alternative sets of probes that specifically recognize mutant and wild type ROD1 alleles.

If the plant is homozygous for the mutant ROD1 gene or the corresponding wild type ROD1 gene, the diagnostic hybridization assays described above will give rise to a single specific hybridization product, such as one or more hybridizing DNA (restriction) fragments, typical, preferably typical in length, for either the mutant or wild type ROD1 allele. If the plant is heterozygous for the mutant ROD1 allele, two specific hybridization products will appear, reflecting both the hybridization of the mutant and the wild type ROD1 allele.

Identification of the wild type and mutant ROD1 specific hybridization products can occur e.g. by size estimation after gel or capillary electrophoresis (e.g. for mutant ROD1 alleles comprising a number of inserted or deleted nucleotides which results in a size difference between the hybridizing DNA (restriction) fragments from the wild type and the mutant ROD1 allele, such that said fragments can be visibly separated on a gel); by evaluating the presence or absence of the two different specific hybridization products after gel or capillary electrophoresis, whereby the diagnostic hybridization of the mutant ROD1 allele can, optionally, be performed separately from the diagnostic hybridization of the wild type ROD1 allele; by direct sequencing of the hybridizing DNA (restriction) fragments; or by fluorescence-based detection methods.

Furthermore, detection methods specific for a specific mutant ROD1 allele that differ from PCR- or hybridization-based amplification methods can also be developed using the specific mutant ROD1 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant ROD1 allele in biological samples or the determination of the zygosity status of plant material comprising a specific mutant ROD1 allele. More particularly, a preferred embodiment of the kit of the invention comprises at least two specific primers, as described above, for identification of a specific mutant ROD1 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant ROD1 allele therein, as described above, for identification of a specific mutant ROD1 allele, or at least two or three specific probes for the determination of the zygosity status. Optionally, the kit can further comprise any other reagent (such as but not limited to hybridizing buffer, label) for identification of a specific mutant ROD1 allele in biological samples, using the specific probe.

The kit of the invention can be used, and its components can be specifically adjusted, for purposes of quality control (e.g., purity of seed lots), detection of the presence or absence of a specific mutant ROD1 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant ROD1 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant ROD1 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant ROD1 allele, implying the presence of nucleic acids in the samples. Thus the methods referred to herein for identifying a specific mutant ROD1 allele in biological samples, relate to the identification in biological samples of nucleic acids that comprise the specific mutant ROD1 allele.

Another embodiment provides a chimeric gene comprising the following operably linked elements: a plant-expressible promoter; a DNA region, which when transcribed yields an RNA molecule inhibitory to at least one ROD1 gene, said ROD1 gene encoding a protein having at least 90% sequence identity to SEQ ID No. 2 or SEQ ID No. 4; and optionally a transcription termination and polyadenylation region functional in plant cells.

In again another embodiment, a knock-out allele of a ROD1 gene is provided, wherein the knock-out ROD1 allele is a mutated version of the native ROD1 gene selected from the group consisting of: a nucleic acid molecule which comprises at least 90% sequence identity to SEQ ID No. 1 or SEQ ID No. 3; or a nucleic acid molecule encoding an amino acid sequence comprising at least 90% sequence identity to SEQ ID No. 2 or SEQ ID No. 4, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

The chimeric gene according to the invention can be used to produce plants, such as *Brassica juncea* plants, with increased levels of C18:1 in the seeds, or with decreased levels of C18:2 or SATS in the seeds, or to produce seed oil with increased levels of C18:1, or with decreased levels of C18:2 or SATS.

In a further embodiment, a method is provided for producing oil, comprising harvesting seeds from the plants according to the invention, i.e. *Brassica juncea* plants comprising a knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the *Brassica juncea* plant or a part thereof according to the invention, and preparing the food, feed or industrial product from the plant or part thereof.

Plants according to the invention, such as plants comprising at least one knock-out ROD1 gene or plants comprising an RNA molecule inhibitory to at least one ROD1 gene can further be used to produce seeds, such as seeds with increased levels of C18:1, or seeds with decreased levels of C18:2 or SATS, or to produce seed oil with increased levels of C18:1, or with decreased levels of C18:2 or SATS.

The plants according to the invention may additionally contain an endogenous or a transgene, which confers herbicide resistance, such as the bar or pat gene, which confer resistance to glufosinate ammonium (Liberty®, Basta® or Ignite®); or any modified EPSPS gene, such as the 2mEPSPS gene from maize, or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates. Further, the plants according to the invention may additionally contain an endogenous or a transgene which confers increased oil content or improved oil composition, such as a 12:0 ACP thioesterase increase to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists:

Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin.

Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus pumulis, Bacillus. pumulis* strain GB34.

Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

In some embodiments, the plant cells of the invention, i.e. a plant cell comprising a knock-out rod1 gene or an RNA inhibitory to a ROD1 gene, as well as plant cells generated according to the methods of the invention, may be non-propagating cells.

The obtained plants according to the invention can be used in a conventional breeding scheme to produce more plants with the same characteristics or to introduce the characteristic according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny, or to produce food or feed, such as oil, meal, grain, starch, flour or protein, or an industrial product, such as bio fuel, fiber, industrial chemicals, a pharmaceutical or a neutraceutical, or to produce hybrids of plants obtained by methods of the invention.

All patents, patent applications, and publications or public disclosures (including publications on internet) referred to or cited herein are incorporated by reference in their entirety.

The sequence listing contained in the file named "BCS12-2011_ST25.txt", which is 47.5 kilobytes (size as measured in Microsoft Windows®), contains 14 sequences SEQ ID NO: 1 through SEQ ID NO: 14 and was created on 2 Jul. 2012 is filed herewith by electronic submission and is incorporated by reference herein.

In the description and examples, reference is made to the following sequences:

Sequences

SEQ ID No. 1: cDNA sequence of ROD1-A1 from *Brassica juncea*.
SEQ ID No. 2: protein sequence of ROD1-A1 from *Brassica juncea*.
SEQ ID No. 3: cDNA sequence of ROD1-B1 from *Brassica juncea*.
SEQ ID No. 4: protein sequence of ROD1-B1 from *Brassica juncea*.
SEQ ID No. 5: cDNA sequence of ROD1-A2 from *Brassica juncea*.
SEQ ID No. 6: protein sequence of ROD1-A2 from *Brassica juncea*.
SEQ ID No. 7: cDNA sequence of ROD1-B2 from *Brassica juncea*.
SEQ ID No. 8: protein sequence of ROD1-B2 from *Brassica juncea*.
SEQ ID No. 9: cDNA sequence of ROD1-A3 from *Brassica juncea*.
SEQ ID No. 10: protein sequence of ROD1-A3 from *Brassica juncea*.
SEQ ID No. 11: cDNA sequence of ROD1-B3 from *Brassica juncea*.
SEQ ID No. 12: protein sequence of ROD1-B3 from *Brassica juncea*.
SEQ ID No. 13: cDNA sequence of ROD1-B4 from *Brassica juncea*.
SEQ ID No. 14: protein sequence of ROD1-B4 from *Brassica juncea*.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany. Standard procedures for AFLP analysis are described in Vos et al. (1995, NAR 23:4407-4414) and in published EP patent application EP 534858.

Example 1

Isolation of the DNA Sequences of *Brassica juncea* ROD1 Genes

The *B. juncea* cDNA sequence BjROD1_A1 was obtained by Sequencher mediated assembly of 80 bp sequencing reads retrieved by BLAST analysis of in-house *B. juncea* cv J0005006 sequencing read databases using a ROD1 sequence from the *Brassica napus* A genome as the query.

The *B. juncea* cDNA sequences BjROD1_B1, BjROD1_A2, BjROD1_B2, BjROD1_A3, BjROD1_3, and BjROD1_B4 were obtained by assembly of 80 bp sequencing reads retrieved by running the GeneXpression program with different ROD1 sequences from the *Brassica napus* A and C genome as queries using a *B. juncea* cv J0005006 sequencing read databases.

For the BjROD1 cDNA sequence assemblies the ROD1 cDNAs from *B. napus* cv. PPS02-144B were used as a reference sequence.

Thus, seven cDNAs were identified, three of which were annotated to the A genome and four of which were annotated on the B genome: BjROD1-A1 (SEQ ID No. 1), BjROD1-B1 (SEQ ID No. 3), BjROD1-A2 (SEQ ID No. 5), BjROD1-B2 (SEQ ID No. 7), BjROD1-A3 (SEQ ID No. 9), BjROD1-B3 (SEQ ID No. 11), and BjROD1-B4 (SEQ ID No. 13). It is plausible that a fourth ROD1 gene is present on the A genome (BjROD1-A4), which is homeologous to BjROD1-B4, which has a low or no expression, and has therefore not been identified in the cDNA sequence database.

Example 2

Generation and Isolation of Mutant *Brassica juncea* rod1 Alleles

Mutations in the ROD1 genes from *Brassica juncea* identified in Example 1 are generated and identified as follows:

Seeds are preimbibed for two hours on wet filter paper in deionized or distilled water. Half of the seeds are exposed to 0.8% EMS and half to 1% EMS (Sigma: M0880) and incubated for 4 hours.

The mutagenized seeds (M1 seeds) are rinsed 3 times and dried in a fume hood overnight. M1 plants are grown in soil and selfed to generate M2 seeds. M2 seeds are harvested for each individual M1 plant.

M2 plants, derived from different M1 plants, are grown and DNA samples are prepared from leaf samples of each individual M2 plant.

The DNA samples are screened for the presence of point mutations in the ROD1 genes causing the introduction of STOP codons in the protein-encoding regions of the ROD1 genes, amino acid substitutions, or the disruption of splice sites in the ROD1 mRNA, by direct sequencing by standard sequencing techniques and analyzing the sequences for the presence of the point mutations using the NovoSNP software.

Mutant rod1 alleles have been identified of the BjROD1-A1 gene, the BjROD1-B1, gene, the BjROD1-A2 gene, the BjROD1-B2 gene, the BjROD1-A3 gene, the BjROD1-B3 gene and of the BjROD1-B4 gene.

Example 3

Activity of BjROD1 Alleles in Yeast

The activity of the *Brassica juncea* ROD1-1 and ROD1-2 alleles, as well as mutant alleles thereof, are tested in yeast. Cloning of the ROD1 Alleles in Yeast Expression Vectors BjROD1-A1, BjROD1-B1, BjROD1-A2, BjROD1-B2, BjROD1-A3, BjROD1-B3 and BjROD1-B4 and their mutant alleles are amplified by KOD DNA polymerase (Toyobo Life Science Department, http://www.toyobo-global.com), using primers that created 5' BamHI and 3'EcoRI restriction sites.

Following BamHI and EcoRI double digestion, each product is ligated into the p424GPD vector (ATCC, http://www.atcc.org/), in which the cDNA is expressed under control of the constitutive Glyceraldehyde-3-P dehydrogenase promoter, and then transformed into *E. coli* competent cells (TOP10, Invitrogen). Plasmids with correct inserts confirmed by sequencing are transformed into yeast HJ091 cells (cpt1::LEU2 ept1−), and transformants are selected by synthetic minimal media (SD base) with dropout leucine and tryptophan (DO-Leu/-Trp) (Clontech, http://www.clontech.com).

Activity Testing of the ROD1 Alleles in Yeast

ROD1 activity assay is modified based on Supplementary Information in Lu et al., 2009 (PNAS, 2009,106 (44):18837-18842., S1 Materials and Methods). Yeast cells are inoculated from overnight cultures and grown to mid-log phase (OD600=0.5-1.5) at 30° C. in liquid media SD/-Leu/-Trp. To prepare a total membrane fraction, 100 ml yeast cells are harvested by centrifugation at 1500 g for 5 min. Each cell pellet is washed once with sterile water and then resuspended in ice-cold glucose-Tris-EDTA (GTE) buffer [20% glycerol, 50 mM glucose, 25 mM Tris-HCl, pH 7.4, 10 mM EDTA]. Cells are then vortexed for 30 seconds×8 times with 30 seconds gaps on ice. The resulting homogenate is centrifuged at 2,500 g at 4° C. for 10 min. to pellet cell debris. The supernatant is centrifuged at 100,000 g at 4° C. for 1 h and the membrane pellet is resuspended in 200 µL GTE buffer. The protein concentration is determined by Bradford assay.

The PDCT activities in membrane preparations of HJ091 cells transformed with p424GPD (control) or p424ROD1 and mutant alleles are determined as the amount of [14C] dioleoyl-PC produced from 1,2-dioleoyl-rac-glycerol [14C (U)] ([14C-glycerol]diolein). The substrates of 1.8 nmol (200,000 cpm) [14C-glycerol]diolein (American Radiolabeled Chemicals, Inc. (http://www.arcinc.com) and 0.1 µmol dioleoyl-PC are dried under nitrogen gas and resuspended in 50 µL of 4× reaction buffer [final concentrations: 50 mM 3-(N-morpholino)propanesulfonic acid (MOPS)/NaOH (pH 7.5), 20 mM MgCl2, 0.45% Triton X-100] by 2 minutes sonication in a bath sonicator. Reactions (200 µL) are started by adding 50 ng of microsomal proteins suspended in the GTE buffer. Assays are incubated at 15° C. for 15 min and are terminated by the addition of 3 mL of chloroform/ethanol (2:1, vol./vol.), followed by 1.5 mL of 0.9% KCl. Tubes are mixed by vortexing, and phase separation was facilitated by centrifugation at 2,000 g for 2 min. The aqueous phase is aspirated, and the organic phase is washed twice with 1.5 mL of 40% (vol./vol.) ethanol. Samples are analyzed by TLC on Whatman Partisil® K6 silica gel 60 Å 20×20 cm glass plates (Whatman, http://www.whatman.com) in a solvent system of chloroform/methanol/water (65:25:4, by volume), followed by phosphorimaging analysis (phosphorimager 445 SI, Lab Extreme, Inc, http://www.labextreme.com). Corresponding bands are scraped, and radioactivity is determined by scintillation counting on a TRI-CARB® liquid scintillation analyzer (Packard Instrument Company).

It is found that BjROD1-A1 and BjROD1-B1 have activity, whereas no activity of the other BjROD1 genes and mutant BjROD1-A1 and mutant BjROD1-B1 alleles can be detected.

Example 4

Downregulation of BjROD1 in Brassica juncea

The ROD1 genes are downregulated in *Brassica juncea* using hairpin constructs of ROD1.

Construction of the ROD1 Hairpin Constructs

Host *Escherichia coli* strains are TOP10 (with Gateway entry and expression clones) or DB3.1 (with pHELLS-GATE12 destination vector; Invitrogen). Bacterial cultures are grown at 37° C. in Luria broth medium with appropriate antibiotics.

Generation of ROD1 hpRNA Suppression Constructs:

To specifically knock down the expression of the BjROD1 genes, a hairpin construct is generated which contains at least 20 bp identical to both BjROD1-A1 and BjROD1-B1, or to BjROD1-A1, BjROD1-B1, BjROD1-A2, BjROD1-B2, BjROD1-A3, BjROD1-B3 and of B/ROD1-B4. Therefore, a fragment of BjROD1-A1 is amplified by PCR on BjROD1-A1 DNA as template: The PCR reaction (50 µl) contains 0.3 µM of each primer, 2 ng/µL template DNA, 0.2 mM of dNTP mix, 0.02 unit/µL of KOD DNA polymerase (Toyobo), 5 µl of 10×PCR buffer, and 1.5 mM MgSO4. Programmed cycles are as follows: 2 min initial denaturing step at 95° C.; 40 cycles of 20 s denaturation at 95° C., 15 s annealing at 55° C., 20 s extension at 70° C. PCR products are purified with QIAquick Gel Extraction Kit (QIAGEN) and ligated into the pENTR™/D-TOPO® cloning vector (Invitrogen) to generate entry clones according to the manual's instruction. To generate hairpin constructs, 100 ng BjROD1 entry clone and 150 ng pHELLSGATE12 destination vector are mixed, and LR recombination reaction is conducted using Gateway® LR Clonase™ Enzyme following the manual's instruction (Invitrogen). After transformation into TOP10 competent cells, clones are screened by restriction analysis to identify plasmids with the expected insert in the correct orientation, and are validated by sequencing.

The transformation vectors are obtained by extracting the hairpin region from the above hairpin constructs and placing this cassette into a transformation vector under control of the Cauliflower Mosaic Virus 35S promoter containing bar as selectable marker.

Transformation of *Brassica juncea* with the ROD1 Hairpin Constructs

A DNA fragment comprising the hairpin construct and the bar selectable marker is HPLC purified and used to obtain transformed *Brassica juncea* plants by means of direct gene transfer into cells of *Brassica juncea*, followed by regeneration of transformed plant cells into transgenic fertile *Brassica juncea* plants.

Single-copy regenerated transformation events are backcrossed with a *Brassica juncea* (elite) line. Following 2 rounds of selfing seeds from both homozygous transformation events and wild type segregants are harvested for subsequent seed oil analysis.

Oil Composition in Seeds from *Brassica juncea* Transformed with the ROD1 Hairpin Constructs The fatty acid composition of the seed oil of individual progeny *Brassica juncea* plants for homozygous transformation events and the corresponding wild type segregants as well as a non-transformed reference line is determined by extracting the fatty acyls from the seeds and analyzing their relative levels in the seed oil by capillary gas-liquid chromatography as described in WO09/007091.

It is found that the levels of C18:1 is significantly increased in seed lipids of the plants comprising the hairpin construct as compared to wild-type controls or wild-type segregants. These results show that downregulation of the BjROD1-A1 and BjROD1-B1 alleles, and of the BjROD1-A1, BjROD1-B1, BjROD1-A2, BjROD1-B2, BjROD1-A3, BjROD1-B3 and of BjROD1-B4 alleles contributes significantly to the increase of C18:1 levels in the seed lipid fraction.

Further, it is found that the levels of C18:2 and of saturated fatty acids (SATS; C12:0, C14:0, C16:0, C18:0, C20:0, C22:0 and C24:0) are decreased in seeds of plants comprising the ROD1 hairpin construct as compared to wild-type controls or wild-type segregants.

Example 5

Oil Composition in Brassica juncea Comprising ROD1 Knock-out Alleles

*Brassica juncea* plants comprising mutant ROD1-A1 and ROD1-B1 alleles are crossed. Following 2 rounds of selfing seeds from plants homozygous for ROD1-A1 and ROD1-B1 mutations, for the ROD1-A1 mutation, for the ROD1-B1 mutation or wild type segregants (i.e. not comprising any mutant ROD1 allele that would impact the normal function of a ROD1 protein) are obtained.

Fatty acid composition is determined as described above in F1S2 seeds of the *Brassica juncea* lines with mutant BjROD1-A1, BjROD1-B1, and combinations thereof. For each combination of mutants, oil composition is determined in wild-type segregants not comprising the respective mutations in BjROD1-A1 and BjROD1-B1, in lines homozygous for either the mutant BjROD1-A1 or for the mutant BjROD1-B1 allele, and in lines homozygous for both mutants BjROD1-A1 and BjROD1-B1.

It is found that the levels of C18:1 are increased in lines comprising either the mutant BjROD1-A1, or for the mutant BjROD1-B1 allele, or both mutants BjROD1-A1 and BjROD1-B1 as compared to the wild-type segregant. Further, the levels of C18:2 and of SATS (SATS; C12:0, C14:0, C16:0, C18:0, C20:0, C22:0 and C24:0) are decreased in lines comprising either the mutant BjROD1-A1, or the mutant BjROD1-B1 allele, or both mutants BjROD1-A1 and BjROD1-B1 as compared to the wild-type segregant.

Example 6

Detection and/or Transfer of Mutant ROD1 Alleles into (Elite) Brassica Juncea Lines The mutant ROD1 genes are transferred into (elite) *Brassica juncea* breeding lines by the following method: A plant containing a mutant ROD1 gene (donor plant), is crossed with an (elite) *Brassica juncea* line (elite parent/recurrent parent) or variety lacking the mutant ROD1 gene. The following introgression scheme is used (the mutant ROD1 allele is abbreviated to rod1 while the wild type is depicted as ROD1):

BC1 cross: rod1/rod1 (donor plant)×ROD1/ROD1 (elite parent)
F1 plant: ROD1/rod1
BC2 cross: ROD1/rod1×ROD1/ROD1 (recurrent parent)
BC2 plants: 50% ROD1/rod1 and 50% ROD1/ROD1

The 50% ROD1/rod1 are selected using molecular markers (e.g. AFLP, PCR, Invader™, TaqMan®, KASP assay, and the like; see also below) for the mutant ROD1 allele (rod1).

BC3 cross: ROD1/rod1 (BC1 plant)×ROD1/ROD1 (recurrent parent)

BC3 plants: 50% ROD1/rod1 and 50% ROD1/ROD1

The 50% ROD1/rod1 are selected using molecular markers for the mutant ROD1 allele (rod1).

Backcrossing is repeated until BC4 to BC7.

BC4-7 plants: 50% ROD1/rod1 and 50% ROD1/ROD1

The 50% ROD1/rod1 are selected using molecular markers for the mutant ROD1 allele (rod1). To reduce the number of backcrossings (e.g. until BC4 instead of BC7), molecular markers can be used specific for the genetic background of the elite parent.

BC4-7 S1 cross: ROD1/rod1×ROD1/rod1

BC4-7 S1 plants: 25% ROD1/ROD1 and 50% ROD1/rod1 and 25% rod1/rod1

Plants containing rod1 are selected using molecular markers for the mutant ROD1 allele (rod1). Individual BC4-7 S1 or BC4-7 S2 plants that are homozygous for the mutant ROD1 allele (rod1/rod1) are selected using molecular markers for the mutant and the wild-type ROD1 alleles. These plants are then used for seed production.

To select for plants comprising a point mutation in a ROD1 allele, direct sequencing by standard sequencing techniques known in the art can be used.

Alternatively, Invader™ technology (Third Wave Agbio) can be used to discriminate plants comprising a specific point mutation in an ROD1 allele from plants not comprising that specific point mutation. Discriminating Invader™ probes are thus developed to detect the presence or absence and the zygosity status of mutant alleles identified in Example 3, based on the single nucleotide difference between the mutant and wildtype allele. Briefly, probes specific for the mutant or corresponding wild-type target ROD1 gene and "invading" probes which can be used in combination with them are developed. Generally, each probe set consists of one probe specific for the mutant or the wild type target gene of which the first nucleotide after the "5' flap" sequence matches with the nucleotide difference (the so-called "primary probe") and one probe specific for the nucleotides upstream of the nucleotide difference (the so-called "Invader® oligo"). The last nucleotide of the latter primer may match with the nucleotide difference in the mutant, but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio). The Invader™ assay procedure and interpretation of the data are performed as prescribed by the manufacturer (Third Wave Agbio). Briefly, 5' "flap" nucleotide sequences (flap1 for the mutant allele and flap2 for the wild-type allele) are cleaved from the primary probes in the primary phase of the Invader™ assay and are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target ROD1 gene, respectively.

Alternatively, KASP assays (KBioscience) can be used to discriminate plants comprising a specific point mutation in an ROD1 allele from plants not comprising that specific point mutation. Discriminating primers are developed to detect the presence or absence and the zygosity status of mutant alleles identified in Example 2.

Briefly, forward primers specific for the mutant or corresponding wild-type target ROD1 gene and a reverse primer that can be used in combination with them are developed. The nucleotide at the 3' end of the forward primers corresponds to the nucleotide which differs between the mutant and the corresponding wild-type allele. The primers can be used in combination with fluorescent dyes, such as FAM and VIC according to the protocol as described by the manufacturer (KBioscience).

The invention claimed is:

1. A *Brassica juncea* plant, or a cell, part, seed or progeny thereof, comprising seven ROD1 genes, characterized in that two ROD1 genes are knock-out ROD1 genes, wherein one knock-out ROD1 gene is a knock-out allele of the ROD1 gene encoding a protein having at least 90% sequence identity to SEQ ID No. 2, and wherein one knock-out ROD1 gene is a knock-out allele of the ROD1 gene encoding a protein having at least 90% sequence identity to SEQ ID No. 4.

2. The plant of claim 1 which is homozygous for the knock-out ROD1 genes.

3. A transgenic *Brassica juncea* plant comprising seven ROD1 genes, or a cell, part, seed or progeny thereof, comprising a chimeric gene, said chimeric gene comprising the following operably linked DNA fragments:
   a) a plant-expressible promoter;
   b) a DNA region, which when transcribed yields an RNA molecule inhibitory to at least two ROD1 genes; and optionally
   c) a transcription termination and polyadenylation region functional in plant cells, wherein said RNA molecule is inhibitory to a ROD1 gene encoding a protein having at least 90% sequence identity to SEQ ID No. 2 and to a ROD1 gene encoding a protein having at least 90% sequence identity to SEQ ID No. 4.

4. Seeds from the plant of claim 1, said seeds comprising seven ROD1 genes, characterized in that two ROD1 genes are knock-out ROD1 genes as defined in claim 1; or seeds from the plant of claim 3, said seeds comprising seven ROD1 genes, and comprising a chimeric gene as defined in claim 3.

5. A method for increasing the levels of C 18:1 and/or decreasing the levels of saturated fatty acids in seed oil of a *Brassica juncea* plant comprising seven ROD1 genes, comprising the steps of:
   a) introducing or providing a chimeric gene to a *Brassica juncea* plant cell, to create transgenic cells, said chimeric gene comprising the following operably linked DNA fragments:
   a plant-expressible promoter
   a DNA region, which when transcribed yields an RNA molecule inhibitory to at least two ROD1 genes; and optionally
   a transcription termination and polyadenylation region functional in plant cells; and
   b) regenerating transgenic plants from said transgenic cells wherein said RNA molecule is inhibitory to a ROD1 gene encoding a protein having at least 90% sequence identity to SEQ ID No. 2 and to a ROD1 gene encoding a protein having at least 90% sequence identity to SEQ ID No. 4.

6. A method for increasing the levels of C 18:1 and/or decreasing the levels of saturated fatty acids in seed oil of a *Brassica juncea* plant comprising seven ROD1 genes, comprising the steps of:
   a) treating seeds or plant material with a mutagenic chemical substance or with ionizing radiation;
   b) identifying plants with two mutated ROD1 genes, wherein one ROD1 gene, prior to being mutated, encodes a polypeptide having at least 90% sequence identity to SEQ ID No. 2, and wherein one ROD1 gene, prior to being mutated, encodes a polypeptide having at least 90% sequence identity to SEQ ID No. 4; and
   c) selecting a plant with an increased level of C18:1 in the seeds compared to a plant in which the ROD1 gene is not mutated.

7. A method for obtaining a *Brassica juncea* plant with increased levels of C18:1 and/or decreased levels of saturated fatty acids in the seeds comprising the step of introducing two knock-out alleles of a ROD1 gene in said *Brassica juncea* plant as defined in claim 1, and selecting said *Brassica juncea* plant with increased levels of C18:1 in the seeds for the presence of said knock-out alleles of a ROD1 gene by analyzing genomic DNA from said plant for the presence of at least one molecular marker, wherein said at least one molecular marker is linked to said knock-out alleles of said ROD1 genes.

8. A method for combining at least two knock-out ROD1 alleles as defined in claim 1 from one *Brassica juncea* plant to another *Brassica juncea* plant comprising the steps of:
   (a) identifying a first *Brassica juncea* plant comprising at least one knock-out ROD1 allele,
   (b) crossing the first *Brassica juncea* plant with a second *Brassica juncea* plant comprising at least one knock-out ROD1 allele and collecting F1 hybrid seeds from the cross,
   (c) optionally, identifying F1 *Brassica juncea* plants comprising the at least two knock-out ROD1 alleles,
   (d) backcrossing F1 *Brassica juncea* plants comprising the at least two knock-out ROD1 alleles with the second *Brassica juncea* plant not comprising the at least two knock-out ROD1 alleles for at least one generation (x) and collecting BCx seeds from the crosses,
   (e) identifying in every generation BCx *Brassica juncea* plants comprising the at least two knock-out ROD1 alleles by analyzing genomic DNA of said BCx plants for the presence of at least two molecular markers, wherein one of the at least two molecular markers is linked to one of said knock-out ROD1 alleles, and wherein the other of the at least two molecular markers is linked to the other of said knock-out ROD1 alleles.

* * * * *